United States Patent
Chang et al.

(10) Patent No.: US 12,110,340 B2
(45) Date of Patent: Oct. 8, 2024

(54) BINDING PROTEINS AND CHIMERIC ANTIGEN RECEPTOR T CELLS TARGETING GASP-1 GRANULES AND USES THEREOF

(71) Applicant: Proplex Technologies, LLC, Dresher, PA (US)

(72) Inventors: Frank N. Chang, Dresher, PA (US); George P. Tuszynski, Pittsgrove, NJ (US); Solomon Luo, Orwigsburg, PA (US); Jeff Yang, Bethesda, MD (US)

(73) Assignee: Proplex Technologies, LLC, Dresher, PA (US)

( * ) Notice: Subject to any disclaimer, the term of this patent is extended or adjusted under 35 U.S.C. 154(b) by 522 days.

(21) Appl. No.: 16/408,510

(22) Filed: May 10, 2019

(65) Prior Publication Data

US 2019/0345256 A1 Nov. 14, 2019

Related U.S. Application Data

(60) Provisional application No. 62/768,325, filed on Nov. 16, 2018, provisional application No. 62/670,182, filed on May 11, 2018.

(51) Int. Cl.

| | |
|---|---|
| *C07K 16/30* | (2006.01) |
| *A61P 35/00* | (2006.01) |
| *C07K 14/705* | (2006.01) |
| *C07K 14/71* | (2006.01) |
| *C07K 14/725* | (2006.01) |
| *C12N 5/0783* | (2010.01) |
| *G01N 33/574* | (2006.01) |

(52) U.S. Cl.
CPC .............. *C07K 16/30* (2013.01); *A61P 35/00* (2018.01); *C07K 14/7051* (2013.01); *C07K 14/70521* (2013.01); *C07K 14/71* (2013.01); *C12N 5/0638* (2013.01); *G01N 33/57488* (2013.01); *G01N 33/57492* (2013.01); *C07K 2317/31* (2013.01); *C07K 2317/34* (2013.01); *C07K 2317/56* (2013.01); *C07K 2317/622* (2013.01); *C07K 2317/76* (2013.01); *C07K 2319/02* (2013.01); *C07K 2319/03* (2013.01)

(58) Field of Classification Search
CPC ................ C07K 16/30; C07K 14/7051; C07K 14/70521; C07K 14/71; C07K 2317/31; C07K 2317/34; C07K 2317/56; C07K 2317/622; C07K 2317/76; C07K 2319/02; C07K 2319/03; C07K 16/28; C07K 2319/33; C07K 14/705; C07K 14/723; C07K 16/18; C07K 2317/24; A61P 35/00; C12N 5/0638; C12N 5/0636; C12N 2501/515; C12N 2510/00; G01N 33/57488; G01N 33/57492; G01N 33/56966; G01N 33/57415; G01N 33/57423; G01N 33/6893; A61K 2039/505

See application file for complete search history.

(56) References Cited

U.S. PATENT DOCUMENTS

| | | | |
|---|---|---|---|
| 8,420,333 B2 | 4/2013 | Chang et al. | |
| 8,980,269 B2 | 3/2015 | Chang et al. | |
| 9,140,704 B2 | 9/2015 | Chang et al. | |
| 9,920,129 B2 | 3/2018 | Aburatani et al. | |
| 2002/0150898 A1 | 10/2002 | Tang et al. | |
| 2003/0064053 A1 | 4/2003 | Liu et al. | |
| 2004/0018181 A1 | 1/2004 | Kufe et al. | |
| 2004/0123343 A1 | 6/2004 | La Rosa et al. | |
| 2004/0142862 A1 | 7/2004 | Whistler et al. | |
| 2008/0171014 A1 | 7/2008 | Wu et al. | |
| 2008/0260740 A1 | 10/2008 | Zhang et al. | |
| 2012/0027780 A1 | 2/2012 | Van Ryn et al. | |
| 2012/0219570 A1* | 8/2012 | Chang | A61P 35/00 424/174.1 |
| 2013/0183317 A1 | 7/2013 | Chang et al. | |

(Continued)

FOREIGN PATENT DOCUMENTS

| | | | |
|---|---|---|---|
| TW | 201400498 A | 1/2014 | |
| WO | 2000029447 A1 | 5/2000 | |
| WO | WO-2011008746 A2 * | 1/2011 | ......... C07K 16/3015 |

(Continued)

OTHER PUBLICATIONS

Chang et al. G Protein Coupled Receptor-Associated Sorting Protein 1 (GASP-1) Granule as a Cancer Invasion and Progression Biomarker (Br. J. Cancer Res. 3(1); 349-356, 2020).*

(Continued)

*Primary Examiner* — Alana Harris Dent
(74) *Attorney, Agent, or Firm* — Buchanan Ingersoll & Rooney PC

(57) ABSTRACT

A method for detecting cells having granules expressing G protein coupled receptor-associated sorting protein 1 (GASP-1) or a fragment thereof is provided. The detection method may comprise: (a) contacting the cells with an effective amount of a binding protein, wherein the binding protein comprises an antigen binding fragment that specifically binds GASP-1; and (b) identifying cells having granules bound to the binding protein. The GASP-1 granules may be in the cytosol or on the surface of the cells. Also provided are methods for producing T-cells comprising a chimeric antigen receptor, anti-GASP-1 antibody or a bi-specific binding protein. Further provided are methods for treating GASP-1-mediated to disease or inactivating exosomes, microvesicles or oncosomes.

45 Claims, 10 Drawing Sheets

Specification includes a Sequence Listing.

(56) References Cited

U.S. PATENT DOCUMENTS

2014/0193420 A1    7/2014    Aburatani et al.
2016/0299143 A1   10/2016   Weinhausel et al.

FOREIGN PATENT DOCUMENTS

| | | |
|---|---|---|
| WO | 2011025962 A1 | 3/2011 |
| WO | 2012144208 A1 | 10/2012 |
| WO | 2016201300 A1 | 12/2016 |
| WO | 2017172981 A2 | 10/2017 |

OTHER PUBLICATIONS

American Lung Association, 4 pages ((last updated Oct. 1, 2021).*
Yoshinaga et al., (J. Biochem 143(5): 593-601, published online Jan. 23, 2008).*
Almagro & Fransson, Frontiers in Bioscience 2008; 13:1619-33 (see Section 3 "Antibody Structure and the Antigen Binding Site" and Figure 1).*
De Genst et al., (Developmental and Comparative Immunology 30:187-198, 2006).*
Taiwan Office Action with Search Report for Taiwan Application No. 108116302, dated Mar. 2, 2021, 10 pages.
American Cancer Society; Cancer Facts & Figures 2018. Available at:http://www.cancer.org/research/cancerfactsstatistics/cancerfactsfigures2018/index.
Bardelli et al., Cancer Cell 31, 172-179 (2017).
Bettegowda et al., Sci. Transl. Med. 6, 224ra24 (2014).
Chen et al., PLoS One9:e95240 (2014).
Cohen et al., Proc. Natl. Acad. Sci. U.S.A. 114, 10202-10207 (2017).
Cohen et al., Science, Feb. 23, 2018: vol. 359, Issue 6378, pp. 926-930 (2018).
Hogendorf et al., Disease Markers, vol. 2017, Article ID 8629712 (2017).
Horgan, J., Scientific American, Jun. 14, 2017, 10 pages.
Kwapisz, D., Ann. Transl. Med. 5(3):46. (2017).
McFarland et al., Cancer Res; 77(18);4763-72. ©2017 AACR.
Melo et al., Nature. 523.7559 (Jul. 9, 2015):p. 177.
Neumann et al., Comput. Struct. Biotechnol. J.;16:190-195 (2018).
Sasaroli et al., Biomarkers in Medicine. 3 (3):275-288 (2009).
Torga et al., JAMA Oncol. 2018;4(6):868-870.
Valenzuela et al., Cancer Microenviron. 2015;8:65-73.
Villalobos et al., Hematol. Oncol. Clin. North Am. Feb. 2017;31(1):13-29.
Xie et al., Journal of Translational Medicine, 2011;9(1):43.
International Preliminary Report on Patentability and Written Opinion for International Application No. PCT/US2019/031556, issued Nov. 17, 2020, 14 pages.
International Search Report and Written Opinion for International Application No. PCT/US19/31556, mailed Sep. 17, 2019, 19 pages.
Cho et al., British Journal of Pharmacology, 168:1355-1374 (2013).
Marley et al., PloS One, 5(2):e9325, pp. 1-9 (2010).
Uniprot Submission A2MY50_MOUSE, Anti-acid phosphatase variable light chain 11, Feb. 20, 2007, [retrieved on Sep. 3, 2019], Retrieved from the internet: <URL:https://www.uniprot.org/uniprot/A2MY50>.
Uniprot Submission R7NBY4_9FIRM, HTH cro/C1-type domain-containing protein, Nov. 22, 2017, [retrieved on Sep. 3, 2019], Retrieved from the internet: <URL:https://www.uniprot.org/uniprot/R7NBY4>.
Tuszynski et al., "G-protein coupled receptor-associated sorting protein 1 (GASP-1), a potential biomarker in breast cancer," Jul. 23, 2011, vol. 91(2), pp. 608-613, XP028302943, Experimental and Molecular Pathology.
Zheng et al., "G-protein coupled receptor-associated sorting protein 1 (GASP-1), a ubiquitous tumor marker," Aug. 1, 2012, vol. 93(1), pp. 111-115, XP055175336, Experimental and Molecular Pathology.
Extended European Search Report for European Application No. 19 799 602.8, dated Dec. 14, 2021, 10 pages.
Wang et al., "The diagnostic value of serum tumor markers CEA, CA19-9, CA125, CA15-3, and TPS in metastatic breast cancer," Clinica Chimica Acta 470 (2017) 51-55.
Korean Request for the Submission of an Opinion for Korean Application No. 10-2020-7035644, dated Sep. 25, 2023 with translation, 13 pages.

\* cited by examiner

Lane M: DNA marker
Lane 1: VL
Lane 2: VH

BINDING PROTEINS AND CHIMERIC ANTIGEN RECEPTOR T CELLS TARGETING GASP-1 GRANULES AND USES THEREOF

CROSS-REFERENCE TO RELATED APPLICATIONS

This application claims the benefit of U.S. Provisional Application No. 62/670,182, filed May 11, 2018 and U.S. Provisional Application No. 62/768,325, filed Nov. 16, 2018, the contents of each of which are incorporated herein by reference in their entireties for all purposes.

FIELD OF THE INVENTION

The invention relates to granules expressing G protein coupled receptor-associated to sorting protein 1 (GASP-1), also called GASP-1 granules, binding proteins and chimeric antigen receptor T (CAR-T) cells targeting the GASP-1 granules, and uses of the binding proteins and the CAR-T cells for cancer detection and treatment.

BACKGROUND OF THE INVENTION

Cancer is the second most common cause of death in the United States and is exceeded only by heart disease. Cancer morbidity increases significantly if it is not detected early in its progression. Early detection of cancer before symptoms appear is the most effective deterrent against cancer. For example, colorectal cancer incidence rates have been decreasing for most of the past two decades (from 66.3 cases per 1,000,000 persons in 1985 to 45.3 in 2007) due to colorectal cancer screening tests that allow the detection and removal of colorectal polyps before they progress to cancer.

Extracellular vesicles (EV) released from cancer cells have been implicated in cancer progression and metastasis. The EVs include exosomes (about 30-100 nm in diameter), microvesicles (about 100-1000 nm in diameter), and large oncosomes (about 1-10 µm in diameter). Exosomes originate from multivesicular bodies (MVB) of the late endocytic pathway and are released by fusion with cell membrane. Microvesicles and oncosomes, on the other hand, are released by budding from cell membrane.

Overexpression of GASP-1 is required for both cancer initiation and cancer progression. For example, in knockdown experiments using triple negative breast cancer (TNBC) cells, cells expressing low levels of GASP-1 grew much more slowly than wild type cells. When GASP-1 is completely downregulated, the cells die and cannot be propagated.

In pursuit of safe and effective cancer therapies, researchers have sought to identify antigens that are found only on cancer cells but not on healthy cells. The quest for such tumor-specific antigens (TSAs) has not been successful. Current CAR-T therapies are targeting biomarkers that are only preferentially present on cancer cell surfaces meaning that they are also present on normal cells. This has resulted in unwanted and severe side effects. Additionally, current CAR-T treatment is only effective against hematological tumors and not solid tumors. Several reasons contribute to current ineffective CAR-T therapies against solid tumors. First, solid tumors are heterogeneous. Unlike the cancerous B cells, which have CD19 pretty much across the board on their surfaces, not all solid tumor cells necessarily carry the antigen that CAR-T cells are designed to attack. Secondly, even if a single-target CAR-T therapy is successful in eradicating tumors, cancers can sometimes return after having shed that antigen. Thirdly, a solid tumor contains a solid mass of cells that have hundreds or even thousands of layers thick making it difficult for CAR-T cells to infiltrate.

There remains a need for effective cancer treatment by targeting cancer cells, especially those in a solid tumor, with minimum side effects on normal cells.

SUMMARY OF THE INVENTION

The present invention provides a novel method for identifying and treating cancer patients by targeting granules expressing G protein coupled receptor-associated sorting protein 1 (GASP-1), also known as GASP-1 granules, for example, in the cytosol or on the surface of the cells.

A method for detecting cells having granules expressing G protein coupled receptor-associated sorting protein 1 (GASP-1) or a fragment thereof is provided. The detection method comprises contacting the cells with an effective amount of a binding protein, and identifying cells having granules bound to the binding protein. The binding protein comprises an antigen binding fragment that specifically binds GASP-1. The identified cells are cells having GASP-1 granules. The binding protein may be a humanized antibody or a chimeric antigen receptor (CAR).

According to the detection method, the GASP-1 granules in the cells may have a diameter in the range from 0.1 to 5.0 µm. The average number of the GASP-1 granules in the cells may be in the range from 20 to 150 per cell. The GASP-1 granules may be in the cytosol or the surface of the cells.

According to the detection method, the cells may be in a tumor. The tumor may be a solid tumor or hematological tumor. The cells may be cancer cells.

According to the detection method, the cells may be in a subject having cancer. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. The cancer may be selected from the group consisting of bladder cancer, breast cancer, colon cancer, glioblastoma, liver cancer, lung cancer, melanoma, ovarian cancer, pancreatic cancer and prostate cancer. The breast cancer may be high grade ductal carcinoma in situ (DCIS) breast cancer or triple negative breast cancer. The lung cancer may be non-small cell lung cancer (NSCLC). The subject may have received a cancer treatment.

The detection method may further comprise detecting a cancer biomarker in the cells. The cancer biomarker may be selected from the group consisting of CA125, CA19-9, CA15-3, CA27.29, AFP, BRCA1/BRCA2, EGFR, HER-2, KIT and CEA.

A binding protein is provided. The binding protein comprises an anti-GASP-1 single-chain variable fragment (anti-GASP-1 scFv). The anti-GASP-1 scFv may comprise a variable heavy (VH) chain and a variable light (VL) chain.

The VH chain may comprise an amino acid sequence of SEQ ID NO: 1. The VH chain may comprise a first complementarity-determining region 1 (VHCDR1) consisting of the amino acid sequence of SEQ ID NO: 2, a second complementarity-determining region 2 (VHCDR2) consisting of the amino acid sequence of SEQ ID NO: 3, a third complementarity-determining region 3 consisting of the amino acid sequence of SEQ ID NO: 4 (VCCDR3), or a combination thereof.

The VL chain may comprise SEQ ID NO: 9 or 17. The VL chain may comprise a first complementarity-determining region (VL1CDR1) consisting of the amino acid sequence of SEQ ID NO: 10 or 18, a second complementarity-determining region (VL1CDR2) consisting of the amino acid sequence of SEQ ID NO: 11, and a third complementarity-determining region (VL1CDR3) consisting of the amino acid sequence of SEQ ID NO: 12.

In the binding protein, the VH chain may be connected to the VL chain with a linker. The linker may comprise the amino acid sequence of SEQ ID NO: 21.

The anti-GASP-1 scFv may bind specifically an immunodominant epitope of GASP-1 and the immunodominant epitope may comprise the amino acid sequence of SEQ ID NO: 22.

The binding protein may be an antibody selected from the group consisting of a recombinant monoclonal antibody, a polyclonal antibody, a humanized antibody and an antigen binding fragment thereof. The binding protein may be a humanized antibody.

The binding protein may be a chimeric antigen receptor (CAR) comprising the anti-GASP-1 scFv. The anti-GASP-1 scFv may comprise an amino acid sequence selected from the group consisting of SEQ ID NOs: 36 and 43.

The binding protein may comprise at least one amino acid sequence selected from the group consisting of SEQ ID NOs: 1-4, 9-12 and 17-18.

The binding protein may be conjugated with a chemotherapeutic agent. The chemotherapeutic agent may be selected from the group consisting of Anastrozole, Exemestane, Letrozole, Palbociclib, Ribociclib, Neratinib, Abemaciclib, Olaparib, Regorafenib, Tretinoin, axicabtagene ciloleucel, Dasatinib, Nilotinib, Bosutinib, Ibrutinib, Idelalisib, Venetoclax, Ponatinib, Midostaurin, Enasidenib, Tisagenlecleucel, Ivosideni, Duvelisib, Imatinib, Gefitinib, Erlotinib, Lapatinib, Sorafenib, Abiraterone, Critozinib, Vemurafenib, radioactive isotopes such as $^{111}$In and $^{90}$Y, toxins such as auristatins, maytansinoids, doxorubicin, taxols, cisplatin, vinblastine, calicheamicin, and *Pseudomonas* exotoxin A.

A method for producing T cells comprising a chimeric antigen receptor (CAR-T cells) is provided. The CAR-T cell production method comprises introducing into T cells a gene encoding a CAR comprising an anti-GASP-1 single-chain variable fragment (anti-GASP-1 scFv), expressing the anti-GASP-1 scFv by the T cells, and isolating T cells expressing the anti-GASP-1 scFv. The anti-GASP-1 scFv may comprise an amino acid sequence selected from the group consisting of SEQ ID NOs: 36 and 43.

A method for producing an anti-GASP-1 antibody is provided. The anti-GASP-1 antibody production method comprises immunizing a host with a GASP-1 peptide as an immunogen. The GASP-1 peptide may comprise the amino acid sequence of SEQ ID NO: 22.

A method for producing a bi-specific binding protein is provided. The bi-specific binding protein production method comprises combining the binding protein of the present invention with an additional humanized antibody. The resulting bi-specific binding protein shows better immunotherapy specificity and/or efficacy than the humanized antibody. The binding protein may be a humanized GASP-1 antibody or a chimeric antigen receptor (CAR). The additional humanized antibody may be selected from the group consisting of Rituximab, Alemtuzumab, Adalimumab, Efalizumab, Cetuximab, Bevacizumab, Natalizumab, Panitumumab, Ranibizumab, Ipilimumab, Belimumab, Obinutuzumab, Pertuzumab, Vedolizumab, Ramucirumab, Evolocumab, Pembrolizumab, Nivolumab, Atezolizumab, Reslizumab, Necitumumab, Trastuzumab, Pertuzumab, Ofatumumab, Durvalumab, Bortezomib, Elotuzumab, Avelumab, Cemiplimab, and Olaratumab.

For each bi-specific binding protein preparation method, a bi-specific binding protein as prepared is provided.

A pharmaceutical composition is provided. The pharmaceutical composition comprises the binding protein or bi-specific binding protein of the present invention, and a pharmaceutically acceptable carrier.

A method for treating a GASP-1-mediated disease or disorder in a subject in need thereof is provided. The treatment method comprises administering to the subject an effective amount of the pharmaceutical composition of the present invention. The GASP-1-mediated disease or disorder may be a tumor. The tumor may be a solid tumor. The tumor may be a hematological tumor. The GASP-1-mediated disease or disorder may be cancer.

The subject may have received a treatment of cancer. The GASP-1 may be expressed in granules in cells of the subject. The GASP-1 granules may be in the cytosol or on the surface of the cells.

A method for inhibiting growth of cells expressing GASP-1 is provided. The inhibition method comprises administering to the cells an effective amount of the pharmaceutical composition of the present invention. The cells may be cancer cells. The cells may be in a patient having cancer.

A method for inactivating exosomes, microvesicles, or oncosomes expressing GASP-1 is provided. The inactivation method comprises administering to the exosomes, microvesicles, or oncosomes an effective amount of the pharmaceutical composition of the present invention. The exosomes, microvesicles, or oncosomes may be in a subject having cancer. The exosomes, microvesicles, or oncosomes may be in blood circulation of the subject. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. The cancer may be selected from the group consisting of bladder cancer, breast cancer, colon cancer, glioblastoma, liver cancer, lung cancer, melanoma, ovarian cancer, pancreatic cancer and prostate cancer. The breast cancer may be high grade ductal carcinoma in situ (DCIS) breast cancer or triple negative breast cancer. The lung cancer may be non-small cell lung cancer (NSCLC).

DETAILED DESCRIPTION OF THE INVENTION

Figure 1:
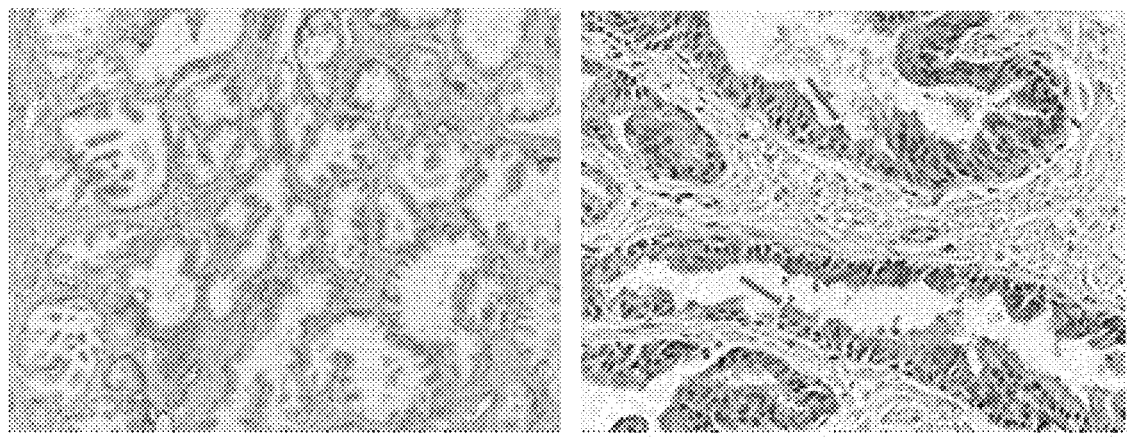
FIG. 1 shows extracellular oncosomes released from prostate cancer cells via membrane blebs protruding from cell membrane (right panel) but not from normal prostate cells (left panel).

The present invention provides a binding protein comprising an anti-G protein coupled receptor-associated sorting protein 1 (GASP-1) single-chain variable fragment (scFv) and the uses of the anti-GASP-1 scFv for detecting cells expressing GASP-1 or a fragment thereof, for example, in or on the surface of granules in the cells, and for producing antibodies or T cells comprising a chimeric antigen receptor (CAR-T) for targeting GASP-1 expressing cancer cells. The invention is based on the inventors' surprising discovery of anti-GASP-1 single-chain variable fragments (scFv) as well as granules highly enriched with GASP-1 (GASP-1 granules). The GASP-1 granules are of different sizes, ranging from powdery granules, fine granules, to coarse granules whose surfaces are not smooth. The size of coarse granules may be about several hundred times that of the powdery granules. GASP-1 granules have been found widely distributed inside or on cell membrane of cancer cells, for example, underneath the cell membrane, in the cytosol, clustered around nucleus or inside the nucleus. The GASP-1 granules of various sizes have been found in cells from breast, triple negative, prostate, lung, liver, pancreatic, ovarian, glioblastoma, bladder, melanoma, or colon cancer.

The inventors have also surprisingly discovered that as cancer progresses, the GASP-1 granules may increase in both numbers and sizes. At an early stage of cancer, the GASP-1 granules may be predominantly of powdery to fine granules. At a late stage of highly invasive and aggressive cancer such as triple negative breast cancer (TNBC) and glioblastoma, GASP-1 granules may be primarily coarse GASP-1 granules.

In normal cells, GASP-1 may be only minimally expressed or not expressed in the cytosol and, if present, may be in a powdery form. The GASP-1 granules may be minimally present in the cytosol of normal cells but not present on cell membrane. The GASP-1 granules may be present in nuclei of some normal cells. The surprising discovery of the presence of the GASP-1 granules only on the surface of cancer cells but not normal cells provides a first example of a tumor-specific antigen (TSA). This discovery makes GASP-1 an ideal target for cancer immunotherapies using, for example, either CAR-T cells or a humanized monoclonal antibody containing a GASP-1 scFv sequence because targeting the GASP-1 granules for cancer treatment would have minimum side effects on normal cells.

The terms "granules expressing G protein coupled receptor-associated sorting protein 1 (GASP-1)" and "GASP-1 granules" are used herein interchangeably and refer to granules containing GASP-1 or a fragment thereof. Depending upon their sizes, there are three forms of GASP-1 granules: powdery, fine and coarse granules.

The term "powdery GASP-1 granules" as used herein refers to GASP-1 granules having a diameter in the range from 0.1 to 0.4 μm. The term "fine GASP-1 granules" as used herein refers to GASP-1 granules having a diameter in the range of 0.4-1.0 μm. The term "coarse GASP-1 granules" as used herein refers to GASP-1 granules having a diameter in the range of 1.0-5.0 μm. The GASP-1 coarse granules are larger in diameter than the extracellular microvesicles. The GASP-1 granules may be in the cytosol or on the surface of the cells. The GASP-1 granules may be endosomes.

The terms "single-chain Fv" and "scFv" are used herein interchangeably and refer to a single chain peptide comprising a VH chain and a VL chain of an antibody against an antigen. For example, an anti-GASP-1 scFv refers to a single peptide comprising a VH chain and a VL chain of an anti-GASP-1 antibody. The scFv may further comprise a polypeptide linker between the VH and VL chains, enabling the scFv to form a desired structure for binding the antigen. Where the antibody is a humanized antibody, the single-chain peptide comprising the VH and VL chains of the antibody is a human single-chain Fv or hscFv.

The term "microvesicles" as used herein refers to extracellular vesicles (EV) formed by cell membrane and released from cell membrane surface of cells, for example, cancer cells. The microvesicles have a diameter of 0.1-1 μm. The microvesicles are present in biological fluids such as blood, saliva, urine, and cerebrospinal fluid. The microvesicles may express GASP-1.

The term "exosomes" as used herein refers to extracellular vesicles (EV) originating from multivesicular bodies (MVB) of the late endocytic pathway and are released by fusion with cell membrane. The exosomes have a diameter of 30-100 nm. The exosomes are present in biological fluids such as blood, saliva, urine, and cerebrospinal fluid. The exosomes may express GASP-1.

The term "oncosomes" as used herein refers to extracellular vesicles (EV) formed by cell membrane and released from cell membrane surface of cells, for example, cancer cells. The oncosomes have a diameter of 1-10 μm. The oncosomes are present in biological fluids such as blood, saliva, urine, and cerebrospinal fluid. The oncosomes may express GASP-1.

The term "an effective amount" as used herein refers to an amount of a pharmaceutical composition comprising a binding protein or a bi-specific binding protein required to achieve a stated goal (e.g., detecting cells having GASP-1 granules, treating a GASP-1-mediated disease or disorder in a subject in need thereof, inhibiting growth of cells expressing GASP-1, and inactivating exosomes, microvesicles or oncosomes). The effective amount of the pharmaceutical composition may vary depending upon the stated goals and the physical characteristics of the composition.

A method for detecting cells having granules expressing G protein coupled receptor-associated sorting protein 1 (GASP-1) or a fragment thereof is provided. The detection method comprises contacting the cells with an effective amount of a binding protein, and identifying cells having granules bound to the binding protein. The binding protein comprises an antigen binding fragment that specifically binds GASP-1. The identified cells are cells having GASP-1 granules.

According to the detection method, the GASP-1 granules may be in the cytosol or on the surface of the cells. In one embodiment, the GASP-1 granules may be in the cytosol of the cells. In another embodiment, the GASP-1 granules are on the surface of the cells. In yet another embodiment, the GASP-1 granules may not be in the nuclei of the cells.

According to the detection method, the number of the GASP-1 granules in the cells may vary. There may be about 10-1,000, 20-500, or 20-200 GASP-1 granules per cell. The average number of the GASP-1 granules in the cells is in the range from 20 to 150. The GASP-1 granules may be of different sizes, ranging from powdery granules, fine granules, to coarse granules. The coarse GASP-1 granules may be at least 10, 50, 100 or 500 times larger than the powdery granules in the same cell. The GASP-1 granules may have a diameter in the range of about 0.1-10, 0.1-0.4, 0.4-1.0, 1.0-5.0, 0.1-1.0, 0.1-5.0, 0.4-5.0, 0.2-10, 0.2-3.0, 0.2-5.0, 0.5-1.0 or 0.5-5.0 µm. In one embodiment, the GASP-1 granules have a diameter in the range from 0.2 to 3.0 µm. We have discovered that as cancer progresses, more coarse GASP-1 granules are found which could either be due to maturation of powdery (and/or fine granules) or to aggregation of these GASP-1 granules. In one embodiment, at least 30%, 40%, 50%, 60%, 70%, 80% or 90% of the GASP-1 granules may be coarse GASP-1 granules in cancer cells. At least 30%, 40%, 50%, 60%, 70%, 80% or 90% of the GASP-1 granules may be coarse GASP-1 granules in cells from cancers that are more aggressive, for example, high grade DCIS, triple negative breast cancer and glioblastoma. The coarse GASP-1 granules may be clustering around nuclear membrane and/or on cell membrane.

According to the detection method, the cells having GASP-1 granules may be in a tumor. The tumor may be a solid tumor or hematological tumor. The tumor may be in a subject. The subject may have cancer. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. For example, the cancer may be bladder cancer, breast cancer, colon cancer, glioblastoma, liver cancer, lung cancer, melanoma, ovarian cancer, pancreatic cancer or prostate cancer. The breast cancer may be high grade ductal carcinoma in situ (DCIS) breast cancer or triple negative breast cancer. The lung cancer may be non-small cell lung cancer (NSCLC). The subject may have received a cancer treatment.

According to the detection method, the cells having GASP-1 granules may be cancer cells. The cells may be in a subject. The subject may have cancer. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. For example, the cancer may be bladder cancer, breast cancer, colon cancer, glioblastoma, liver cancer, lung cancer, melanoma, ovarian cancer, pancreatic cancer or prostate cancer. The breast cancer may be high grade ductal carcinoma in situ (DCIS) breast cancer or triple negative breast cancer. The lung cancer may be non-small cell lung cancer (NSCLC). The subject may have received a cancer treatment.

The detection method may further comprise detecting a cancer biomarker in the cells having GASP-1 granules or GASP-1 or a fragment thereof. The cancer biomarker may be any suitable biomarker for bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor or stomach adenocarcinoma. For example, the cancer may be bladder cancer, breast cancer, colon cancer, glioblastoma, liver cancer, lung cancer, melanoma, ovarian cancer, pancreatic cancer or prostate cancer. The breast cancer may be high grade ductal carcinoma in situ (DCIS) breast cancer or triple negative breast cancer. The lung cancer may be non-small cell lung cancer (NSCLC). Exemplary cancer biomarkers include CA125, CA19-9, CA15-3, CA27.29, AFP, BRCA1/BRCA2, EGFR, HER-2, KIT, VEGF, KRAS, ALK, PSA, HE4, CYFRA 21-1, NSE, PD-L1, TIMP-1, TIMP-2, HGF, OPN, MSLN, MMP2 and CEA.

According to the detection method, the binding protein may comprise an anti-GASP-1 single-chain variable fragment (anti-GASP-1 scFv). The binding protein may be an anti-GASP-1 antibody or a chimeric antigen receptor (CAR). The anti-GASP-1 antibody is an antibody capable of binding to GASP-1 or its fragment, for example, a GAPS-1 peptide of EEASPEAVAGVGFESK (SEQ ID NO: 22). The anti-GASP-1 antibody may be a recombinant antibody or an antigen-binding fragment thereof. The antibody may be a monoclonal antibody, a polyclonal antibody or a humanized antibody.

A binding protein comprising an anti-GASP-1 single-chain variable fragment (anti-GASP-1 scFv) is also provided. The anti-GASP-1 scFv comprises a variable heavy (VH) chain and a variable light (VL) chain. The binding protein may be an antibody or a chimeric antigen receptor (CAR).

The VH chain of the anti-GASP-1 scFv may comprise the amino acid sequence of SEQ ID NO: 1. The VH chain may consist of the amino acid sequence of SEQ ID NO: 1. The VH chain may comprise a first complementarity-determining region 1 (VHCDR1), a second complementarity-determining region 2 (VHCDR2) and a third complementarity-determining region 3 (VHCDR3). The VHCDR1 may comprise the amino acid sequence of SEQ ID NO: 2. The VHCDR1 may consist of the amino acid sequence of SEQ ID NO: 2. The VHCDR2 may comprise the amino acid sequence of SEQ ID NO: 3. The VHCDR2 may consist of the amino acid sequence of SEQ ID NO: 3. The VHCDR3 may comprise the amino acid sequence of SEQ ID NO: 4. The VHCDR3 may consist of the amino acid sequence of SEQ ID NO: 4. The VHCDR1 may be encoded by a nucleotide sequence comprising SEQ ID NO: 6. The VHCDR1 may be encoded by the nucleotide sequence of SEQ ID NO: 6. The VHCDR2 may be encoded by a nucleotide sequence comprising SEQ ID No: 7. The VHCDR2 may be encoded by the nucleotide sequence of SEQ ID No: 7. The VHCDR3 may be encoded by a nucleotide sequence comprising SEQ ID NO: 8. The VHCDR3 may be encoded by the nucleotide sequence of SEQ ID NO: 8.

The VL chain of the anti-GASP-1 scFv may comprise the amino acid sequence of SEQ ID NO: 9. The VL chain may consist of the amino acid sequence of SEQ ID NO: 9. The VL chain may comprise a first complementarity-determining region 1 (VLCDR1), a second complementarity-determining region 2 (VLCDR2) and a third complementarity-determining region 3 (VLCDR3). The VLCDR1 may comprise the amino acid sequence of SEQ ID NO: 10. The VLCDR1 may consist of the amino acid sequence of SEQ ID NO: 10. The VL1CDR2 may comprise the amino acid sequence of SEQ ID NO: 11. The VL1CDR2 may consist of the amino acid sequence of SEQ ID NO: 11. The VL1CDR3 may comprise the amino acid sequence of SEQ ID NO: 12. The VL1CDR3 may consist of the amino acid sequence of SEQ ID NO: 12.

The VL chain of the anti-GASP-1 scFv may comprise the amino acid sequence of SEQ ID NO: 17. The VL chain may consist of the amino acid sequence of SEQ ID NO: 17. The VL chain may comprise a first complementarity-determining region 1 (VLCDR1), a second complementarity-determining region 2 (VLCDR2) and a third complementarity-determining region 3 (VLCDR3). The VLCDR1 may comprise an amino acid sequence of SEQ ID NO: 18. The VLCDR1 may consist of the amino acid sequence of SEQ ID NO: 18. The VL1CDR2 may comprise the amino acid sequence of SEQ ID NO: 11. The VL1CDR2 may consist of the amino acid sequence of SEQ ID NO: 11. The VL1CDR3 may comprise the amino acid sequence of SEQ ID NO: 12. The VL1CDR3 may consist of the amino acid sequence of SEQ ID NO: 12.

The anti-GASP-1 scFv may comprise a variable heavy (VH) chain encoded by the nucleotide sequence of SEQ ID NO: 5 and a variable light (VL) chain encoded by the nucleotide sequence of SEQ ID NO: 13. The VH chain may be connected to the VL chain with a linker consisting of the amino acid sequence of SEQ ID NO: 21. The anti-GASP-1 scFv may be an antibody selected against an immunodominant epitope of GASP-1 consisting of the amino acid sequence of SEQ ID NO: 22.

The anti-GASP-1 scFv may comprise a variable heavy (VH) chain encoded by the nucleotide sequence of SEQ ID NO: 5 and a variable light (VL) chain encoded by the nucleotide sequence of SEQ ID NO: 19. The VH chain may be connected to the VL chain with a linker consisting of the amino acid sequence of SEQ ID NO: 21. The anti-GASP-1 scFv may be an antibody selected against an immunodominant epitope of GASP-1 consisting of the amino acid sequence of SEQ ID NO: 22.

The anti-GASP-1 scFv may comprise a variable heavy (VH) chain consisting of the amino acid sequence of SEQ ID NO: 1, and a variable light (VL) chain consisting of the amino acid sequence of SEQ ID NO: 9. The VH chain may be connected to the VL chain with a linker consisting of the amino acid sequence of SEQ ID NO: 21. The anti-GASP-1 scFv may be selected against an immunodominant epitope of GASP-1 consisting of the amino acid sequence of SEQ ID NO: 22.

The anti-GASP-1 scFv may comprise a variable heavy (VH) chain consisting of the amino acid sequence of SEQ ID NO: 1, and a variable light (VL) chain consisting of the amino acid sequence of SEQ ID NO: 17. The VH chain may be connected to the VL chain with a linker consisting of the amino acid sequence of SEQ ID NO: 21. The anti-GASP-1 scFv may be selected against an immunodominant epitope of GASP-1 consisting of the amino acid sequence of SEQ ID NO: 22.

The VH chain of the anti-GASP-1 antibody or scFv may comprise a CDR1 consisting of the amino acid sequence of SEQ ID NO: 2, a CDR2 consisting of the amino acid sequence of SEQ ID NO: 3, and a CDR3 consisting of the amino acid sequence of SEQ ID NO: 4.

The VH chain of the anti-GASP-1 antibody or scFv may comprise a CDR1 encoded by the nucleotide sequence of SEQ ID NO: 6, a VHCDR2 encoded by the nucleotide sequence of SEQ ID No: 7, and a VHCDR3 encoded by the nucleotide sequence of SEQ ID NO: 8.

The VL chain of the anti-GASP-1 scFv may comprise a CDR1 consisting of the amino acid sequence of SEQ ID NO: 10, a CDR2 consisting of the amino acid sequence of SEQ ID NO: 11, and a CDR3 consisting of the amino acid sequence of SEQ ID NO: 12.

The VL chain of the anti-GASP-1 scFv may comprise a CDR1 encoded by the nucleotide sequence of SEQ ID NO: 14, a CDR2 encoded by the nucleotide sequence of SEQ ID NO: 15, and a CDR3 encoded by the nucleotide sequence of SEQ ID NO: 16.

The VL chain of the anti-GASP-1 scFv may comprise a CDR1 consisting of the amino acid sequence of SEQ ID NO: 18, a CDR2 consisting of the amino acid sequence of SEQ ID NO: 11, and a CDR3 consisting of the amino acid sequence of SEQ ID NO: 12.

The VL chain of the anti-GASP-1 scFv may comprise a CDR1 encoded by the nucleotide sequence of SEQ ID NO: 20, a CDR2 encoded by the nucleotide sequence of SEQ ID NO: 15, and a CDR3 encoded by the nucleotide sequence of SEQ ID NO: 16.

In the binding protein, the VH chain may be connected to the VL chain with a linker. The linker may comprise the amino acid sequence of SEQ ID NO: 21. The linker may consist of the amino acid sequence of SEQ ID NO: 21.

The anti-GASP-1 scFv may bind specifically an immunodominant epitope of GASP-1. The immunodominant epitope may comprise the amino acid sequence of SEQ ID NO: 22. The immunodominant epitope may consist of the amino acid sequence of SEQ ID NO: 22.

The binding protein may be an antibody selected from the group consisting of a recombinant monoclonal antibody, a polyclonal antibody, a humanized antibody and an antigen binding fragment thereof. In one embodiment, the binding protein may be a humanized antibody.

The binding protein may be an anti-GASP-1 antibody, may be an antibody capable of binding to GASP-1 or its fragment, for example, a GASP-1 peptide of EEASPEAVAGVGFESK (SEQ ID NO: 22). The anti-GASP-1 antibody may be a recombinant antibody or an antigen-binding fragment thereof. The antibody may be a monoclonal antibody, a polyclonal antibody or a humanized antibody.

The binding protein may be a chimeric antigen receptor (CAR), comprising the anti-GASP-1 scFv. The anti-GASP-1 scFv may comprise the amino acid sequence comprising SEQ ID NO: 36. The anti-GASP-1 scFv may consist of the amino acid sequence of SEQ ID NO: 36. The anti-GASP-1 scFv may comprise the amino acid sequence comprising SEQ ID NO: 43. The anti-GASP-1 scFv may consist of the amino acid sequence of SEQ ID NO: 43.

The binding protein may comprise at least one amino acid sequence selected from the group consisting of SEQ ID NOs: 1-4, 9-12 and 17-18. The binding protein may comprise amino acid sequences of SEQ ID NOs: 1 and 9. The binding protein may comprise amino acid sequences of SEQ ID NOs: 1 and 17. The binding protein may comprise amino acid sequences of SEQ ID NOs: 2-4. The binding protein may comprise amino acid sequences of SEQ ID NOs: 10-12. The binding protein may comprise amino acid sequences of SEQ ID NOs: 11, 12 and 18. The binding protein may comprise amino acid sequences of SEQ ID NOs: 1 and 10-12. The binding protein may comprise amino acid sequences of SEQ ID NOs: 1, 11, 12 and 18. The binding protein may comprise amino acid sequences of SEQ ID NOs: 2-4 and 9. The binding protein may comprise amino acid sequences of SEQ ID NOs: 2-4 and 17.

The binding protein may be conjugated with a chemotherapeutic agent. The chemotherapeutic agent may be selected from the group consisting of Anastrozole, Exemestane, Letrozole, Palbociclib, Ribociclib, Neratinib, Abemaciclib, Olaparib, Regorafenib, Tretinoin, axicabtagene ciloleucel, Dasatinib, Nilotinib, Bosutinib, Ibrutinib, Idelalisib, Venetoclax, Ponatinib, Midostaurin, Enasidenib, Tisagenlecleucel, Ivosideni, Duvelisib, Imatinib, Gefitinib, Erlotinib, Lapatinib, Sorafenib, Abiraterone, Critozinib, Vemurafenib, radioactive isotopes such as $^{111}$In and $^{90}$Y, toxins such as auristatins, maytansinoids, doxorubicin, taxols, cisplatin, vinblastine, calicheamicin, and *Pseudomonas* exotoxin A.

A method for producing T cells comprising a chimeric antigen receptor (CAR-T cells) is provided. The CAR-T cell production method comprises introducing into T cells a gene encoding a CAR. The CAR comprises the anti-GASP-1 single-chain variable fragment (anti-GASP-1 scFv) of the present invention. The CAR production method further comprises expressing the anti-GASP-1 scFv by the T cells and isolating T cells expressing the anti-GASP-1 scFv.

According to the CAR-T cell production method, the anti-GASP-1 scFv may comprise the amino acid sequence of SEQ ID NO: 36. The anti-GASP-1 scFv may consist of the amino acid sequence of SEQ ID NO: 36. The anti-GASP-1 scFv may comprise the amino acid sequence of SEQ ID NO: 43. The anti-GASP-1 scFv may consist of the amino acid sequence of SEQ ID NO: 43.

The CAR may further comprise a signal peptide (SEQ ID NO: 35), a CD8 hinge (SEQ ID NO: 37), a CD28 transmembrane intracellular domain (SEQ ID NO: 38), a CD3 zeta (SEQ ID NO: 39), T2A (SEQ ID NO: 36) and EGFRt (SEQ ID NO: 41). Elements such as interleukins, chemokines, immune checkpoint inhibitors, may enhance the efficacy of the CAR-T if they are co-expressed. Using interleukin-12 (IL-12) as an example, the CAR sequence can be CAR-T2A-EGFRt-T2A-IL-12, CAR-T2A-EGFRt-IRES-IL-12 or CAR-T2A-EGFRt-T2A-PGK promoter-IL-12. The co-stimulatory domains can be 4-1BB, OX40, etc. these elements may improve the CAR-T treatment as well. The co-stimulatory domains (4-1BB, OX40, etc.) can be added to the co-stimulatory domain of the CAR, including the following examples:
  (a) a CD8 hinge, a CD28 transmembrane, 4-1BB intracellular domain, a CD3 zeta;
  (b) a CD8 hinge, a CD8 transmembrane, 4-1BB intracellular domain, a CD3 zeta;
  (c) a CD8 hinge, a CD28 transmembrane, OX40 intracellular domain, a CD3 zeta;
  (d) a CD8 hinge, a CD8 transmembrane, OX40 intracellular domain, a CD3 zeta; and
  (e) a CD8 hinge, a CD28 transmembrane intracellular domain, 4-1BB or OX40, a CD3 zeta.

In view that the currently available CAR-T therapies are rather ineffective against solid tumors, GASP-1 CAR-T therapy may be combined with currently approved CAR-T treatments such as tisagenlecleucel (Kymriah) or axicabtagene ciloleucel (Yescarta), which go after cells producing CD19, to improve effectiveness of such CAR-T treatments. GASP-1 CAR-T containing an additional CAR sequence directed against CD19 or another cancer surface antigen may also be used. A combination of GASP-1 CAR-T with another immunotherapy called a checkpoint inhibitor is also suggested. The checkpoint inhibitor may be Ipilimumab, Nivolumab, Pembrolizumab, Atezolizumab, Avelumab, Durvalumab or Cemiplimab.

A method for producing an anti-GASP-1 antibody is provided. The antibody production method comprises immunizing a host with a GASP-1 peptide as an immunogen. The GASP-1 peptide may be any peptide derived from GASP-1. The GASP-1 peptide may comprise an amino acid sequence selected from the group consisting of SEQ ID NOs: 22-26. The GASP-1 peptide may consist of an amino acid sequence selected from the group consisting of SEQ ID NOs: 22-26. The GASP-1 peptide may comprise the amino acid sequence of SEQ ID NO: 23. The GASP-1 peptide may consist of the amino acid sequence of SEQ ID NO: 23. The GASP-1 peptide may comprise the amino acid sequence of SEQ ID NO: 24. The GASP-1 peptide may consist of the amino acid sequence of SEQ ID NO: 24. The GASP-1 peptide may comprise the amino acid sequence of SEQ ID NO: 25. The GASP-1 peptide may consist of the amino acid sequence of SEQ ID NO: 25. The GASP-1 peptide may comprise the amino acid sequence of SEQ ID NO: 26. The GASP-1 peptide may consist of the amino acid sequence of SEQ ID NO: 26.

A method for producing a bi-specific binding protein. The bi-specific binding protein production method comprises combining the binding protein of the present invention with an additional humanized antibody to produce a bi-specific binding protein. The bi-specific binding protein may have better immunotherapy specificity and/or efficacy than the additional humanized antibody. The binding protein may be a GASP-1 antibody or CAR of the present invention. The additional humanized antibody may be selected from the group consisting of Rituximab, Alemtuzumab, Adalimumab, Efalizumab, Cetuximab, Bevacizumab, Natalizumab, Panitumumab, Ranibizumab, Ipilimumab, Belimumab, Obinutuzumab, Pertuzumab, Vedolizumab, Ramucirumab, Evolocumab, Pembrolizumab, Nivolumab, Atezolizumab, Reslizumab, Necitumumab, Trastuzumab, Pertuzumab, Ofatumumab, Durvalumab, Bortezomib, Elotuzumab, Avelumab, Cemiplimab, and Olaratumab.

For each bi-specific binding protein production method, the produced bi-specific binding protein is provided. The bi-specific binding protein comprises a binding protein of the present invention and an additional humanized antibody. The bi-specific binding protein may have better immunotherapy specificity and/or efficacy than the additional humanized antibody. The binding protein may be a GASP-1 antibody or CAR of the present invention. The additional humanized antibody may be selected from the group consisting of Rituximab, Alemtuzumab, Adalimumab, Efalizumab, Cetuximab, Bevacizumab, Natalizumab, Panitumumab, Ranibizumab, Ipilimumab, Belimumab, Obinutuzumab, Pertuzumab, Vedolizumab, Ramucirumab, Evolocumab, Pembrolizumab, Nivolumab, Atezolizumab, Reslizumab, Necitumumab, Trastuzumab, Pertuzumab, Ofatumumab, Durvalumab, Bortezomib, Elotuzumab, Avelumab, Cemiplimab, and Olaratumab.

For each binding protein or bi-specific binding protein of the present invention, a pharmaceutical composition is provided. The pharmaceutical composition comprises the binding protein or the bi-specific binding protein of the present invention, and a pharmaceutically acceptable carrier.

A method for treating a GASP-1-mediated disease or disorder in a subject in need thereof is provided. The treatment method comprises administering an effective amount of the pharmaceutical composition of the present invention to the subject.

According to the treatment method, the GASP-1-mediated disease or disorder may be a tumor. The tumor may be a solid tumor. The tumor may be a hematological tumor.

According to the treatment method, the GASP-1-mediated disease or disorder may be cancer. The subject may have received a treatment of the cancer. The GASP-1 may be expressed in granules in cells of the subject. The GASP-1 granules may be in the cytosol or on the surface of the cells. In one embodiment, the GASP-1 granules may be in the cytosol of the cells. In another embodiment, the GASP-1 granules may be on the surface of the cells. In another embodiment, the GASP-1 granules may not be in the nuclei of the cells.

The treatment method may further comprise determining the average number, and/or the average diameter, and/or the stability of the GASP-1 granules in the cells of the subject before a cancer treatment. The treatment method may further comprise determining the average number, the average diameter, and/or the stability of the GASP-1 granules in the cells of the subject after the cancer treatment, and optionally comparing the average number, the average diameter, and/or the stability of the GASP-1 granules in the cells of the subject before the cancer treatment with that after the cancer treatment.

According to the treatment method, the cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. The cancer may be selected from the group consisting of bladder cancer, breast cancer, colon cancer, glioblastoma, liver cancer, lung cancer, melanoma, ovarian cancer, pancreatic cancer and prostate cancer. The breast cancer may be high grade ductal carcinoma in situ (DCIS) breast cancer or triple negative breast cancer. The lung cancer may be non-small cell lung cancer (NSCLC).

A method for inhibiting growth of cells expressing GASP-1 is provided. The inhibition method comprises administering an effective amount of the pharmaceutical composition of the present invention to the cells. The cells may be cancer cells. The cells may be in a patient having cancer. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. The cancer may be selected from the group consisting of bladder cancer, breast cancer, colon cancer, glioblastoma, liver cancer, lung cancer, melanoma, ovarian cancer, pancreatic cancer and prostate cancer. The breast cancer may be high grade ductal carcinoma in situ (DCIS) breast cancer or triple negative breast cancer. The lung cancer may be non-small cell lung cancer (NSCLC).

A method for inactivating exosomes, microvesicles, or oncosomes expressing GASP-1 provided. The inactivation method comprises administering an effective amount of the pharmaceutical composition of the present invention to the exosomes, microvesicles, or oncosomes. The inactivation of the exosomes, microvesicles, or oncosomes may be evidenced by a decrease in the number of surface biomarkers such as CD63, CD9 or CD81 for exosomes; CD45, CD47 for microvesicles; and heat shock proteins HSPA5 and HSPA9 for oncosomes. The exosomes, microvesicles, or oncosomes may be in a subject having cancer.

The exosomes, microvesicles, or oncosomes may be in blood circulation of the subject. The cancer may be selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma. The cancer may be selected from the group consisting of bladder cancer, breast cancer, colon cancer, glioblastoma, liver cancer, lung cancer, melanoma, ovarian cancer, pancreatic cancer and prostate cancer. The breast cancer may be high grade ductal carcinoma in situ (DCIS) breast cancer or triple negative breast cancer. The lung cancer may be non-small cell lung cancer (NSCLC).

Example 1. Identification of GASP-1 Oncosomes or Microvesicles in Prostate Cancer GASP-1 expression in prostate cancer cells was examined using a polyclonal antibody against EEASPEAV-AGVGFESK (SEQ ID NO: 22). GASP-1 oncosomes or microvesicles were released by budding from cell membrane. As shown in FIG. 1, while normal prostate cells do not release GASP-1 oncosomes or microvesicles (left panel), GASP-1 oncosomes can be seen budding from cell membrane via forming membrane blebs protruding from cancer cell membrane before being released (see arrows in right panel). The oncosomes or microvesicles appeared to originate from GASP-1 initially concentrated in certain regions of the cancer cell membrane. Completely released oncosomes or microvesicles can also be seen near the area of release (right panel).

Example 2. Presence of GASP-1 Granules of Various Sizes in Cancer Cells

GASP-1 expression in various cancer cells was examined using a polyclonal antibody against EEASPEAV-AGVGFESK (SEQ ID NO: 22). Unlike the released extracellular GASP-1 oncosomes described in Example 1 above, granules expressing GASP-1 were found in the cytosol or on the surface of cancer cells including breast, triple negative breast, prostate, lung, liver, ovarian, glioblastoma, gastric, bladder, melanoma or colon cancer. Because GASP-1 overexpression is required for cancer initiation and progression, the production of GASP-1 granules may be a required step for cancer progression.

Figure 2:
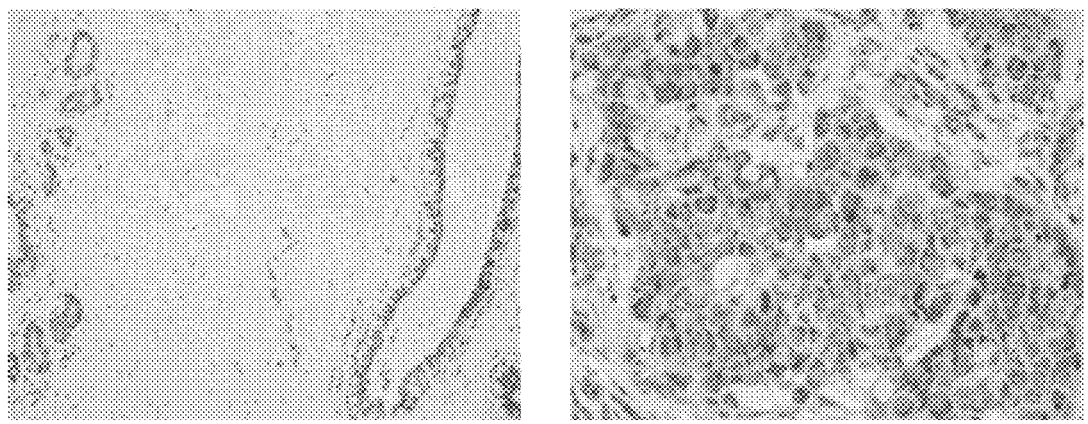
FIG. 2 shows accumulation of GASP-1 granules of different sizes in the cytosol of high grade DCIS breast cancer cells (right panel) but not normal breast cells (left panel).
Figure 3:
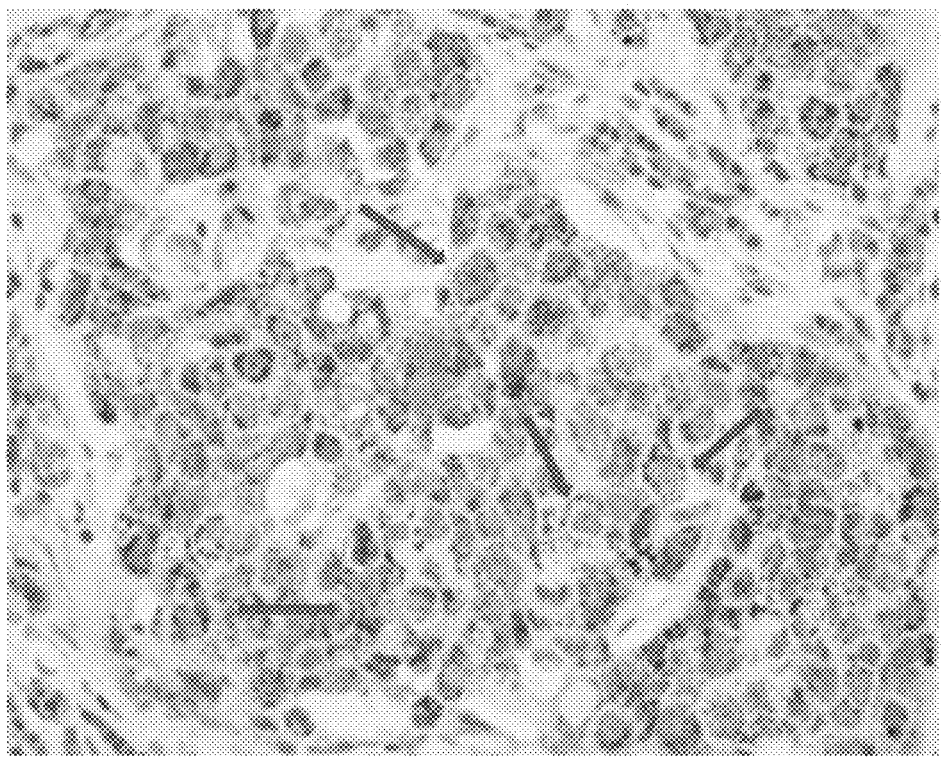
FIG. 3 shows numerous GASP-1 granules attached to the cell membrane or membrane fragments of high grade DCIS breast cancer cells.

FIG. 2 shows immunohistochemistry (IHC) staining of High Grade DCIS Breast Cancer using the polyclonal antibody against EEASPEAVAGVGFESK (SEQ ID NO: 22). In normal breast cells, GASP-1 is only expressed in some nuclei and not in the cytosol (FIG. 2 left panel). In cancer cells, the GASP-1 granules were associated with cell membrane, in the cytosol, clustered around the nuclear membrane and inside the nucleus (FIG. 2 right panel and FIG. 3).

The GASP-1 granules could originate from endosomes. However, unlike endosomes which have a diameter of 0.5 µm when matured, GASP-1 granules of varying sizes ranging from powdery granules, fine granules, to coarse granules are present in this cancer (FIG. 3). The coarse GASP-1 granules with diameter of 1.0 to 5.0 µm may be bigger than the endosomes. Furthermore, unlike the extracellular GASP-1 oncosomes described in FIG. 1, the coarse GASP-1 granules are still attached to the cell membrane (see arrows in FIG. 3) and are not released from the cell membrane. GASP-1 granules also do not form membrane blebs protruding from cell membrane that are the hallmark of oncosomes. The coarse GASP-1 granules are likely formed by either maturation of smaller granules or by aggregation of smaller granules. It is possible that association of so many coarse GASP-1 granules on cell membrane may cause destabilization of the membrane and breaking up (or fragmentation) of cell membranes. The fragmented cell membrane pieces still contain many GASP-1 granules attached to them (FIG. 3). One consequence of breaking up cell membrane would be the release of many GASP-1 granules originally present inside the cell (in the cytosol, clustered on nuclear membrane, or in the nucleus) into tumor microenvironment and later released into blood circulation. We have also found that as cancer becomes more severe, the size of GASP-1 granules becomes bigger and coarse.

The presence of GASP-1 granules on cancer cell surface and absence on normal cell surface offers the opportunity to specifically targeting cancer cells and spare normal cells. The abundant presence of coarse GASP-1 granules on cancer cell surface could also make GASP-1-targeted cancer treatment more effective. In a solid tumor like DCIS breast cancer and other cancers, GASP-1 granules were also found on the surfaces of different cell layers. This would also make immunotherapy targeting GASP-1 granules rather effective because they would be accessible to cancer-treating agents.

Figure 4:
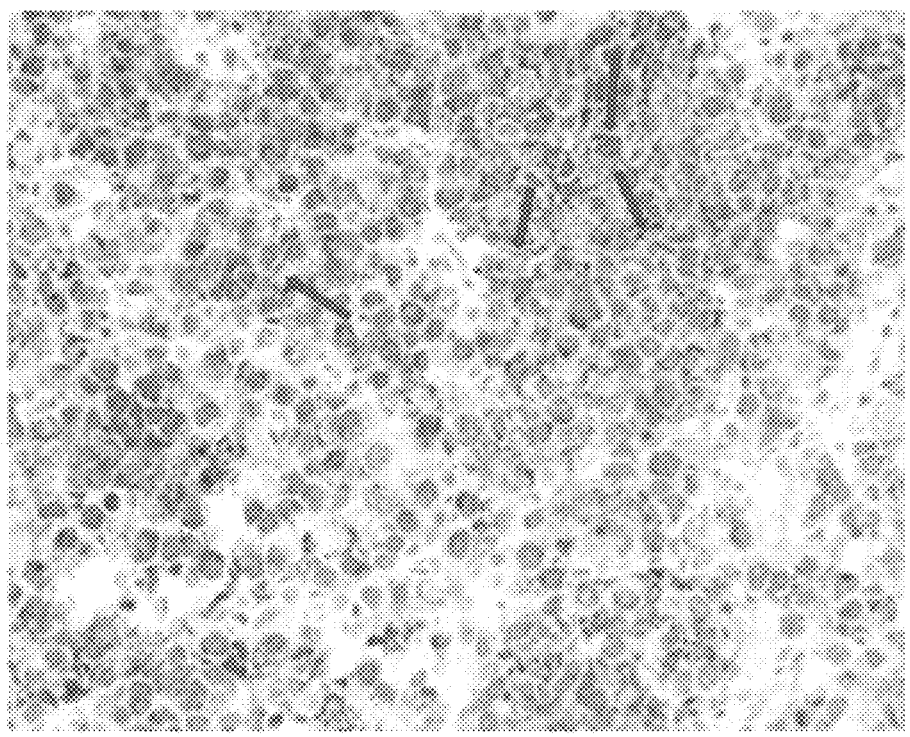
FIG. 4 shows GASP-1 granules of different sizes on the cell membrane of triple negative breast cancer cells.

Triple Negative Breast Cancer, which is a very aggressive form of breast cancer, shows almost identical GASP-1 granular pattern as high grade DCIS (FIG. 4). Again, GASP-1 granules of varying sizes ranging from powdery granules, fine granules, to coarse granules are present in this cancer. The arrows point to GASP-1 granules still attached to cell membrane or membrane fragments.

Figure 5:
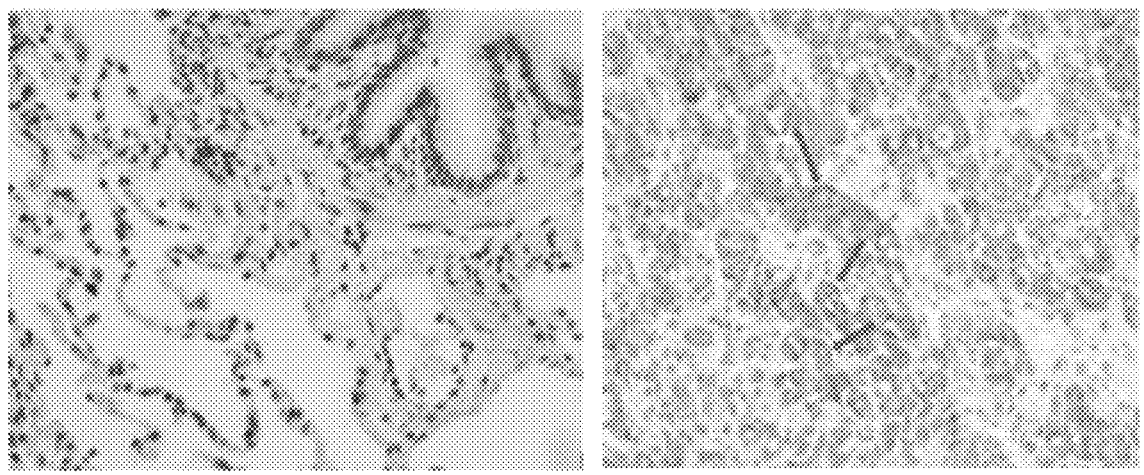
FIG. 5 shows accumulation of GASP-1 granules of different sizes in the cytosol of non-small cell lung cancer (NSCLC) cells (right panel) but not normal lung cells (left panel).

Lung cancer is among the most deadly cancers for both men and women. Its death rate exceeds that of the three most common cancers (colon, breast, and pancreatic) combined. Non-small cell lung cancer (NSCLC) accounts for about 85% of all lung cancer cases and most of newly diagnosed lung cancer patients are late stage. Early detection is very important and with availability of biopsy sample, the presence and abundance of GASP-1 granules in the cytosol could represent early detection. FIG. 5 shows a representative IHC staining of NSCLC. While in normal lung cells, GASP-1 granules are only present in some nuclei and not in the cytosol (left panel), GASP-1 granules of various sizes are present in the cytosol, or attached to the cell membrane in NSCLC (right panel). Arrows in the right panel point out the association of GASP-1 granules with cell membrane and membrane fragments. Therefore, IHC staining of lung tissues for GASP-1 granules from individuals suspecting of lung cancer would confirm the presence of lung cancer.

Figure 6:
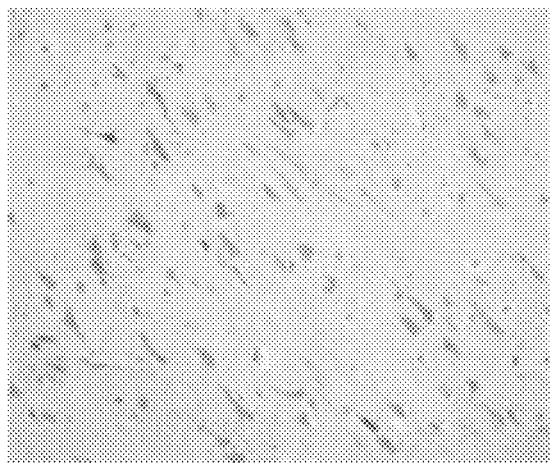
FIG. 6 shows accumulation of GASP-1 granules in the cytosol and on the cell membrane of glioblastoma cells (right panel) but not in normal brain cells (left panel).
Figure 6:
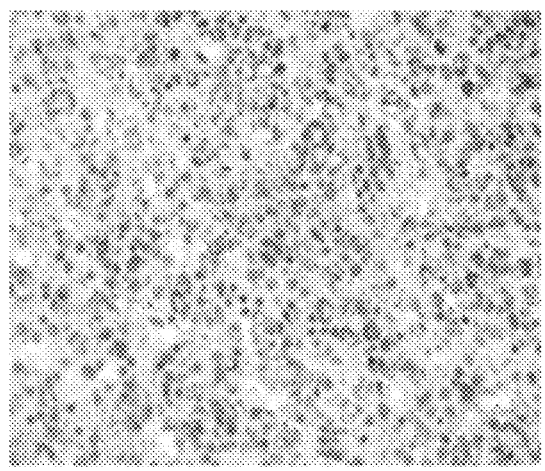

FIG. 6 shows GASP-1 granules in glioblastoma cells. While GASP-1 granules were absent from normal brain cells (left panel), there were highly abundant in glioblastoma cells (right panel). GASP-1 granules of various sizes are present in the cytosol and on the surface of the glioblastoma cells.

Similar large amounts of GASP-1 granules were found to be present in the cytosol or on the surface of ovarian, colon, melanoma, gastric and prostate cancer cells.

The presence of so many GASP-1 granules of varying sizes inside the cancer cell is unexpected. GASP-1 granules are present on all cancer cell surfaces we studied; it can be assumed that they will also be present in other cancer cell surfaces such as endometrial carcinoma, esophagus squamous cell carcinoma, larynx cancer, mucinous cystadenocarcinoma of ovary, renal cell carcinoma, small bowel malignant stromal tumor, and stomach adenocarcinoma. Thus, GASP-1 is a universal cancer biomarker and GASP-1 granule production may represent a required step in cancer progression. One can therefore use the presence of GASP-1 granules, their subcellular localization, their abundance, etc., to assess cancer and cancer severity.

Example 3. GASP-1 scFv Sequences

Figure 7:
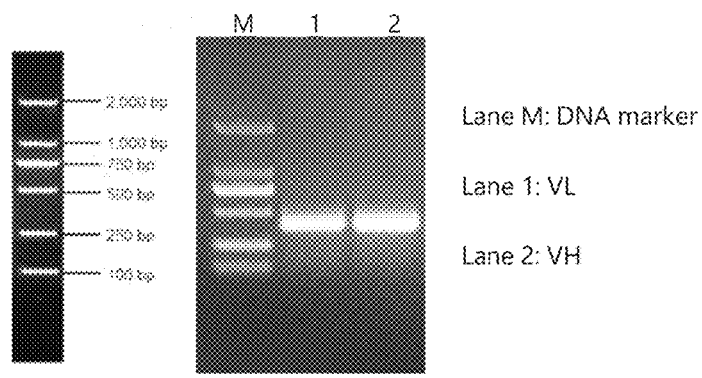
FIG. 7 shows PCR products using VL specific primer (lane 1) or VH specific primer (lane 2). Lane M: 2000 DNA Marker, from top to bottom: 2000, 1000, 750, 500, 250, 100 bp, respectively.

A monoclonal antibody was produced against GASP-1 peptide fragment EEASPEAVAGVGFESK (SEQ ID NO: 22). Several clones were isolated. Clone 14B8 showed the highest titer against the GASP-1 peptide. Cell lysates from clone 14B8 were stored in a TriZol solution. cDNA was reversely transcribed from the total RNA in the cell lysates followed by PCR amplification of the variable regions (both heavy chain (VH) and light chains) of the antibody. FIG. 7 shows the gel analysis of PCR products using VL specific primers (lane 1) or VH specific primers (lane 2). The resulting PCR fragments were then cloned into a standard cloning vector separately and sequenced. Using PCR, the heavy and light chains of clone 14B8 were sequenced, and two variable light chain sequences were found.

Table 1 shows the various amino acid sequences and nucleotide sequences of clone 14B88, for example, the variable heavy (VH) chain, including its first, second and third complementarity-determining regions (VHCDR1, VHCDR2 and VHCDR3), the first variable light (VL1) chain, including its first, second and third complementarity-determining regions (VL1CDR1, VL1CDR2 and VL1CDR3), and the second variable light (VL2) chain, including its first, second and third complementarity-determining regions (VL2CDR1, VL2CDR2 and VL2CDR3). The two light chain sequences differ in only one amino acid in CDR1 (comparing SEQ ID NOs: 9 and 17). The change from N to Y is due to codon change from TAT to AAT as described in SEQ ID: NOs: 13 and 19. This discrepancy might be due to multiple coloniality of the target subclone. The change in the nucleotide and amino acid is highlighted in bold and underlined.

TABLE 1

Sequences of clone 14B8

| No. | Name | Sequence | SEQ ID NO |
|---|---|---|---|
| 1 | VH | EVKLVESGPGLVAPSQSLTITCTVSGFSLTGYGVNWVRQPPGK GLEWLGMIWHNGSTDYNSALRSRLSINKDKSKNQVFLKMNSL QTDDTARYYCARGGRSPWFPYWGQGTLVTVSA | 1 |
| 2 | VHCDR1 | GFSLTGY | 2 |
| 3 | VHCDR2 | WHNGS | 3 |
| 4 | VHCDR3 | GGRSPWFPY | 4 |
| 5 | VH | GAGGTGAAGTTGGTGGAGTCAGGACCTGGCCTGGTGGCGC CCTCACAGAGCCTGACCATCACATGCACCGTCTCAGGGTTC TCATTAACCGGCTATGGTGTAAACTGGGTTCGCCAGCCTCCA GGAAAGGGTCTGGAGTGGCTGGGAATGATCTGGCATAATG GAAGCACAGACTATAATTCAGCTCTCAGATCCAGACTGAGCA TCAACAAGGACAAGTCCAAGAACCAAGTTTTCTTAAAAATGA ACAGTCTGCAAACTGATGACACAGCCAGGTACTACTGTGCC AGAGGGGGAAGGTCCCCCTGGTTTCCTTACTGGGGCCAAG GGACTCTGGTCACTGTCTCTGCA | 5 |
| 6 | VHCDR1 | GGGTTCTCATTAACCGGCTAT | 6 |
| 7 | VHCDR2 | TGGCATAATGGAAGC | 7 |
| 8 | VHCDR3 | GGGGGAAGGTCCCCCTGGTTTCCTTAC | 8 |
| 9 | VL1 | DVVMTQTPLTLSVTIGQPASISCKSSQSLLDSDGKTNLNWLLQ RPGQSPKRLIYLVSKLDSGVPDRFTGSGSGTDFTLKISRVEAD DLGVYYCWQGTHFPWTFGGGTKLEIK | 9 |
| 10 | VL1CDR1 | KSSQSLLDSDGKTNLN | 10 |
| 11 | VL1CDR2 | LVSKLDS | 11 |
| 12 | VL1CDR3 | WQGTHFPWT | 12 |
| 13 | VL1 | GATGTTGTGATGACCCAGACTCCACTCACTTTGTCGGTTACC ATTGGACAACCAGCCTCCATCTCTTGCAAGTCAAGTCAGAGC CTCTTAGATAGTGATGGAAAGACATATTTGAATTGGTTGTTA CAGAGGCCAGGCCAGTCTCCAAAGCGCCTAATCTATCTGGT GTCTAAACTGGACTCTGGAGTCCCTGACAGGTTCACTGGCA GTGGATCAGGGACAGATTTCACACTGAAAATCAGCAGAGTG GAGGCTGACGATTTGGGAGTTTATTATTGCTGGCAAGGTAC ACATTTTCCGTGGACGTTCGGTGGAGGCACCAAGCTGGAAA TCAAA | 13 |
| 14 | VL1CDR1 | AAGTCAAGTCAGAGCCTCTTAGATAGTGATGGAAAGACATAT TTGAAT | 14 |
| 15 | VL1CDR2 | CTGGTGTCTAAACTGGACTCT | 15 |
| 16 | VL1CDR3 | TGGCAAGGTACACATTTTCCGTGGACG | 16 |
| 17 | VL2 | DVVMTQTPLTLSVTIGQPASISCKSSQSLLDSDGKTYLNWLLQ RPGQSPKRLIYLVSKLDSGVPDRFTGSGSGTDFTLKISRVEAD DLGVYYCWQGTHFPWTFGGGTKLEIK | 17 |
| 18 | VL2CDR1 | KSSQSLLDSDGKTYLN | 18 |
| 19 | VL2CDR2 | LVSKLDS | 11 |
| 20 | VL2CDR3 | WQGTHFPWT | 12 |
| 21 | VL2 | GATGTTGTGATGACCCAGACTCCACTCACTTTGTCGGTTACC ATTGGACAACCAGCCTCCATCTCTTGCAAGTCAAGTCAGAGC CTCTTAGATAGTGATGGAAAGACAAATTTGAATTGGTTGTTA CAGAGGCCAGGCCAGTCTCCAAAGCGCCTAATCTATCTGGT GTCTAAACTGGACTCTGGAGTCCCTGACAGGTTCACTGGCA GTGGATCAGGGACAGATTTCACACTGAAAATCAGCAGAGTG GAGGCTGACGATTTGGGAGTTTATTATTGCTGGCAAGGTAC ACATTTTCCGTGGACGTTCGGTGGAGGCACCAAGCTGGAAA TCAAA | 19 |
| 22 | VL2CDR1 | AAGTCAAGTCAGAGCCTCTTAGATAGTGATGGAAAGACAAA TTTGAAT | 20 |

TABLE 1-continued

Sequences of clone 14B8

| No. | Name | Sequence | SEQ ID NO |
|-----|------|----------|-----------|
| 23 | VL2CDR2 | CTGGTGTCTAAACTGGACTCT | 15 |
| 24 | VL2CDR3 | TGGCAAGGTACACATTTTCCGTGGACG | 16 |
| 25 | Linker | GGGGSGGGGSGGGG | 21 |
| 26 | GASP-1 peptide fragment | EEASPEAVAGVGFESK | 22 |
| 27 | GASP-1 peptide fragment | WKEDEAISEATDR | 23 |
| 28 | GASP-1 peptide fragment | CSKSSPKAEEEEV | 24 |
| 29 | GASP-1 peptide fragment | EEASIQAGSQAVEE | 25 |
| 30 | GASP-1 peptide fragment | FWDGKEVSEEAGPC | 26 |

Example 4. Anti-GASP-1 scFv-Fc Proteins

Figure 8:
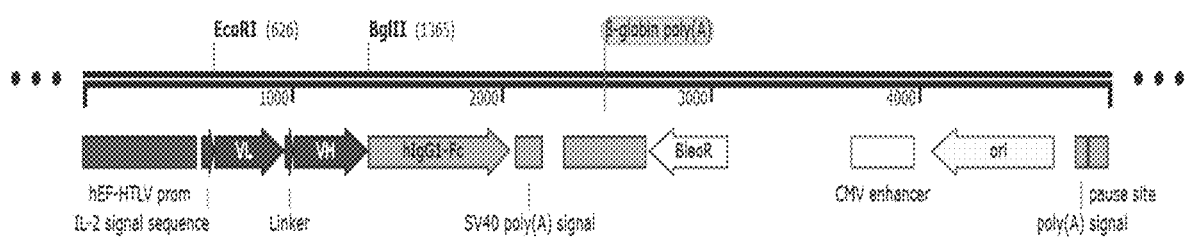
FIG. 8 shows a schematic diagram of scFv1-Fc or scFv2-Fc expression vector of 4911 bp, including a signal sequence, a variable light chain (VL), a linker, a variable heavy chain (VH) and human IgG1 Fc (HIgG1-Fc).
Figure 9:
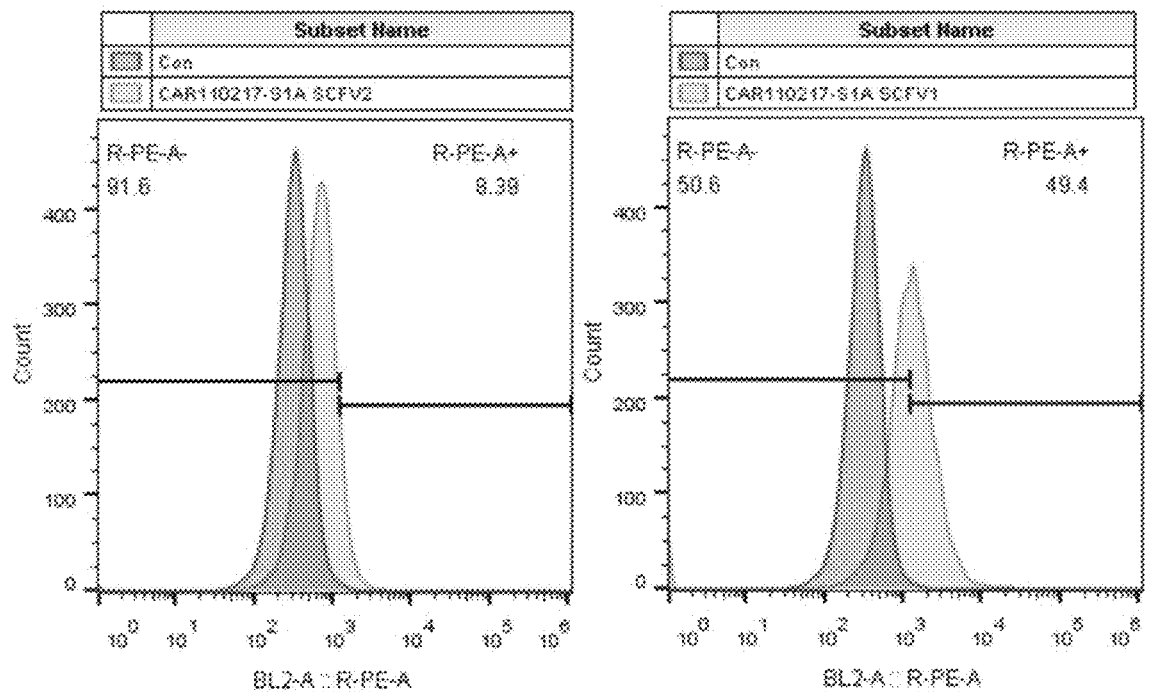
FIG. 9 shows flow cytometric analysis (FACS) of PC3 cells stained with scFv1-Fc (right panel) or scFv2-Fc (left panel) as a primary antibody, and PE-anti-Human IgG Fc antibody as a secondary antibody.

Anti-GASP-1 scFv-Fc proteins were generated based on the sequences of clone 14B8. Using different variable light (VL) chain sequences, two scFv-Fc expression vectors, scFv1-Fc and scFv2-Fc, were prepared. The expression vector construct design is shown in FIG. 8. The VL of scFv1-Fc is the 1468 Light Chain #2 (SEQ ID NO: 9) while the VL of scFv2-Fc is the 1468 Light Chain #1 (SEQ ID NO: 17). The expression vectors were transiently transfected into HEK293 cells, and scFv-Fc proteins were expressed in the HEK293 cells with Gibco® FreeStyle™ 293 Expression Medium.

scFv-Fc proteins were purified by Protein A affinity chromatography and their affinity for target PC-3 cancer cells were analyzed. In flow cytometric analyses (FACS), $5 \times 10^5$ PC-3 cells were stained with either scFv1-Fc or scFv2-Fc protein, followed by PE-anti-Human IgG Fc antibody as the secondary antibody. FIG. 9 shows that 49.4% of the PC-3 cells were recognized by the scFv1-Fc protein while only 8.39% of the PC-3 cells were recognized by the scFv2-Fc protein, indicating that scFv1 has a significant higher affinity for PC-3 cells.

Example 5. GASP-1 Expression on Cancer Cell Surface

Figure 10:
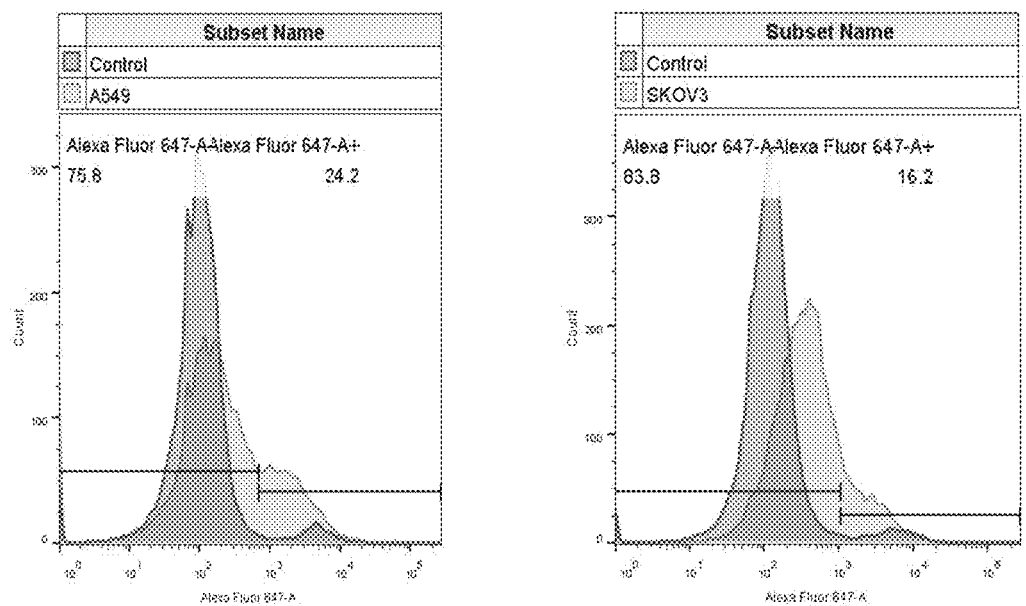
FIG. 10 shows flow cytometric analysis (FACS) of A549 lung cancer cells (left pane) or SKOV3 ovarian cancer cells (right panel) stained with a GASP-1 monoclonal antibody as a primary antibody and an Alexa Fluor-A-anti-Human IgG Fc antibody as a secondary antibody.

Expression of GASP-1 in various cancer cells were studied using an anti-GASP-1 monoclonal antibody against EEASPEAVAGVGFESK (SEQ ID NO: 22). GASP-1 was found on the surface of lung and ovarian cancer cells (FIG. 10). The appearance of GASP-1 on lung cancer surface confirms the result of immunohistochemical (IHC) analysis (FIG. 5) which shows the presence of GASP-1 granules on cancer cell surface. GASP-1 were also found on the surfaces of other cancer cells examined, for example, colon, breast, leukemia, melanoma, glioblastoma and pancreatic cancer cells by flow cytometric analysis. Based on these results, GASP-1 may be a universal cancer biomarker and appears on cell surfaces of other cancers including endometrial carcinoma, esophagus squamous cell carcinoma, glioma, hepatocellular carcinoma, infiltrating ductal breast carcinoma, larynx cancer, renal cell carcinoma, small bowel malignant stromal tumor, and stomach adenocarcinoma. The rather stable association of GASP-1 granules with cell membranes of many cancers would make GASP-1 granules a good target for both CAR-T and humanized recombinant antibodies for treating cancers including many solid tumors.

Example 6. Construction of CAR Vector

Figure 11:
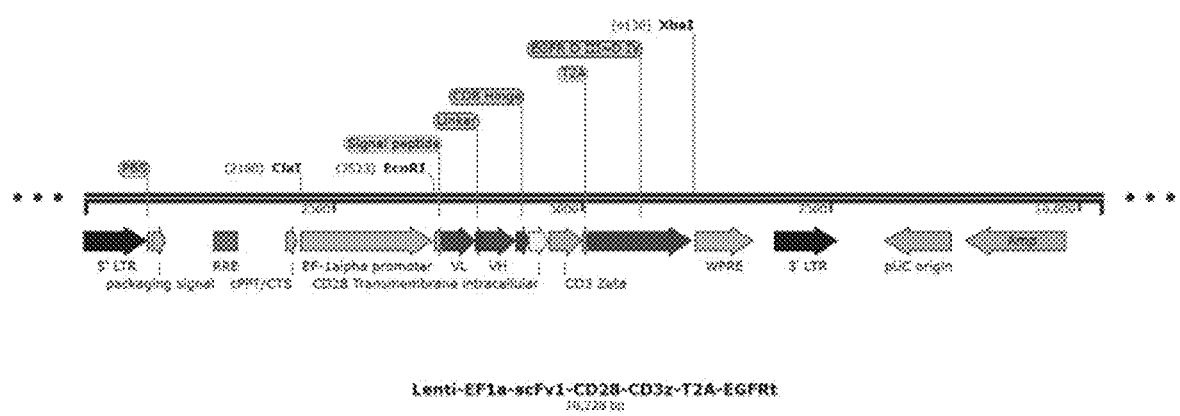
FIG. 11 shows a schematic diagram of a chimeric antigen receptor (CAR) Lenti-EF1a-scFv1-CD28-CD3z-T2A-EGFRt of 10,228 bp.

Because GASP-1 granules are present on the surfaces of different cancer cell layers (see FIG. 3 and FIG. 4), not buried inside cell layers, and are not on normal cell surfaces, a full length of chimeric antigen receptor (CAR) was synthesized with scFv1 and subcloned into lentivirus vector (FIG. 11). The insert was confirmed by Sanger sequencing.

Table 2 shows the nucleotide and amino acid sequences used for the production of CAR cassette. A CAR construct was prepared using nucleotide sequences for the Lenti-EF-1alpha promoter (SEQ ID NO: 27), a signal peptide (SEQ ID NO: 28), scFv1 (SEQ ID NO: 29), CD28 hinge (SEQ ID NO: 30), CD28 intramembrane sequence (SEQ ID NO: 31), CD3z (SEQ ID NO: 32), T2A (thosea asigna virus 2A self-cleaving peptide) (SEQ ID NO: 33) and EGFRt (truncated human epidermal growth factor receptor polypeptide) (SEQ ID NO: 34). The GASP-1 CAR construct comprises amino acid sequences for signal sequence (SEQ ID NO: 35), scFv1 (SEQ ID NO: 36) or scFv2 (SEQ ID NO: 43), CD28 hinge (SEQ ID NO: 37), CD28 transmembrane sequence (SEQ ID NO: 38), CD3z (SEQ ID NO: 39), T2A (SEQ ID NO: 40), and EGFRt (SEQ ID NO: 41). scFv1 may be substituted with scFv2 (SEQ ID NO: 42).

TABLE 2

Sequences of CAR construct

| No. Name | Sequence | SEQ ID NO |
|---|---|---|
| 31 EF-1alpha promoter | GAGTAATTCATACAAAAGGACTCGCCCCTGCCTTGGGGAA TCCCAGGGACCGTCGTTAAACTCCCACTAACGTAGAACCC AGAGATCGCTGCGTTCCCGCCCCCTCACCCGCCCGCTCTC GTCATCACTGAGGTGGAGAAGAGCATGCGTGAGGCTCCG GTGCCCGTCAGTGGGCAGAGCGCACATCGCCCACAGTCC CCGAGAAGTTGGGGGGAGGGGTCGGCAATTGAACCGGTG CCTAGAGAAGGTGGCGCGGGGTAAACTGGGAAAGTGATG TCGTGTACTGGCTCCGCCTTTTTCCCGAGGGTGGGGGAGA ACCGTATATAAGTGCAGTAGTCGCCGTGAACGTTCTTTTTC GCAACGGGTTTGCCGCCAGAACACAGGTAAGTGCCGTGT GTGGTTCCCGCGGGCCTGGCCTCTTTACGGGTTATGGCCC TTGCGTGCCTTGAATTACTTCCACGCCCCTGGCTGCAGTA CGTGATTCTTGATCCCGAGCTTCGGGTTGGAAGTGGGTGG GAGAGTTCGAGGCCTTGCGCTTAAGGAGCCCCTTCGCCTC GTGCTTGAGTTGAGGCCTGGCTTGGGCGCTGGGGCCGCC GCGTGCGAATCTGGTGGCACCTTCGCGCCTGTCTCGCTGC TTTCGATAAGTCTCTAGCCATTTAAAATTTTTGATGACCTG CTGCGACGCTTTTTTTCTGGCAAGATAGTCTTGTAAATGCG GGCCAAGATCTGCACACTGGTATTTCGGTTTTTGGGGCCG CGGGCGGCGACGGGGCCCGTGCGTCCCAGCGCACATGTT CGGCGAGGCGGGGCCTGCGAGCGCGGCCACCGAGAATC GGACGGGGGTAGTCTCAAGCTGGCCGGCCTGCTCTGGTG CCTGGCCTCGCGCCGCCGTGTATCGCCCCGCCCTGGGCG GCAAGGCTGGCCCGGTCGGCACCAGTTGCGTGAGCGGAA AGATGGCCGCTTCCCGGCCCTGCTGCAGGGAGCTCAAAAT GGAGGACGCGGCGCTCGGGAGAGCGGGCGGGTGAGTCA CCCACACAAAGGAAAAGGGCCTTTCCGTCCTCAGCCGTCG CTTCATGTGACTCCACGGAGTACCGGGCGCCGTCCAGGC ACCTCGATTAGTTCTCGAGCTTTTGGAGTACGTCGTCTTTA GGTTGGGGGGAGGGGTTTTATGCGATGGAGTTTCCCCAC ACTGAGTGGGTGGAGACTGAAGTTAGGCCAGCTTGGCAC TTGATGTAATTCTCCTTGGAATTTGCCCTTTTTGAGTTTGG ATCTTGGTTCATTCTCAAGCCTCAGACAGTGGTTCAAAGTT TTTTTCTTCCATTTCAGGTGTCGTGA | 27 |
| 32 Signal peptide | ATGGCCTTACCAGTGACCGCCTTGCTCCTGCCGCTGGCCT TGCTGCTCCACGCCGCCAGGCCG | 28 |
| 33 scFv1 | GATGTTGTGATGACCCAGACTCCACTCACTTTGTCGGTTAC CATTGGACAACCAGCCTCCATCTCTTGCAAGTCAAGTCAG AGCCTCTTAGATAGTGATGGAAAGACATATTTGAATTGGT TGTTACAGAGGCCAGGCCAGTCTCCAAAGCGCCTAATCTA TCTGGTGTCTAAACTGGACTCTGGAGTCCCTGACAGGTTC ACTGGCAGTGGATCAGGGACAGATTTCACACTGAAAATCA GCAGAGTGGAGGCTGACGATTTGGGAGTTTATTATTGCTG GCAAGGTACACATTTTCCGTGGACGTTCGGTGGAGGCACC AAGCTGGAAATCAAAGGTGGAGGTGGCAGCGGAGGAGGT GGGTCCGGCGGTGGAGGAAGCGAGGTGAAGTTGGTGGA GTCAGGACCTGGCCTGGTGGCGCCCTCACAGAGCCTGAC CATCACATGCACCGTCTCAGGGTTCTCATTAACCGGCTAT GGTGTAAACTGGGTTCGCCAGCCTCCAGGAAAGGGTCTG GAGTGGCTGGGAATGATCTGGCATAATGGAAGCACAGAC TATAATTCAGCTCTCAGATCCAGACTGAGCATCAACAAGG ACAAGTCCAAGAACCAAGTTTTCTTAAAAATGAACAGTCTG CAAACTGATGACACAGCCAGGTACTACTGTGCCAGAGGG GGAAGGTCCCCCTGGTTTCCTTACTGGGGCCAAGGGACTC TGGTCACTGTCTCTGCAAGATCT | 29 |
| 34 CD8 hinge | CCACGACGCCAGCGCCGCGACCACCAACACCGGCGCCCA CCATCGCGTCGCAGCCCCTGTCCCTGCGCCCAGAGGCGT GCCGGCCAGCGGCGGGGGGCGCAGTGCACACGAGGGGG CTGGACTTCGCCTGTGATA | 30 |
| 35 CD28 Transmembrane intracellular | TTCTGGGTGCTGGTCGTTGTGGGCGGCGTGCTGGCCTGC TACAGCCTGCTGGTGACAGTGGCCTTCATCATTTTTTGGG TGAGGAGCAAGCGGAGCAGACTGCTGCACAGCGACTACA TGAACATGACCCCCCGGAGGCCTGGCCCCACCCGGAAGC ACTACCAGCCCTACGCCCCTCCCAGGGATTTCGCCGCCTA CCGGAGC | 31 |
| 36 CD3zeta | AGAGTGAAGTTCAGCAGGAGCGCAGACGCCCCCGCGTAC AAGCAGGGCCAGAACCAGCTCTATAACGAGCTCAATCTAG GACGAAGAGAGGAGTACGATGTTTTGGACAAGAGACGTG GCCGGGACCCTGAGATGGGGGGAAAGCCGAGAAGGAAG AACCCTCAGGAAGGCCTGTACAATGAACTGCAGAAAGATA | 32 |

TABLE 2-continued

Sequences of CAR construct

| No. | Name | Sequence | SEQ ID NO |
|---|---|---|---|
|  |  | AGATGGCGGAGGCCTACAGTGAGATTGGGATGAAAGGCG AGCGCCGGAGGGGCAAGGGGCACGATGGCCTTTACCAGG GTCTCAGTACAGCCACCAAGGACACCTACGACGCCCTTCA CATGCAGGCCCTGCCCCCTCGC |  |
| 37 | T2A | GAGGGCAGAGGCAGCCTGCTGACATGTGGCGACGTGGAA GAGAACCCTGGCCCC | 33 |
| 38 | EGFRt | ATGTGGCTGCAGAGCCTGCTGCTCTTGGGCACTGTGGCCT GCAGCATCTCTCGCAAAGTGTGTAACGGAATAGGTATTGG TGAATTTAAAGACTCACTCTCCATAAATGCTACGAATATTA AACACTTCAAAAACTGCACCTCCATCAGTGGCGATCTCCAC ATCCTGCCGGTGGCATTTAGGGGTGACTCCTTCACACATA CTCCTCCTCTGGATCCACAGGAACTGGATATTCTGAAAAC CGTAAAGGAAATCACAGGGTTTTTGCTGATTCAGGCTTGG CCTGAAAACAGGACGGACCTCCATGCCTTTGAGAACCTAG AAATCATACGCGGCAGGACCAAGCAACATGGTCAGTTTTC TCTTGCAGTCGTCAGCCTGAACATAACATCCTTGGGATTAC GCTCCCTCAAGGAGATAAGTGATGGAGATGTGATAATTTC AGGAAACAAAAATTTGTGCTATGCAAATACAATAAACTGGA AAAAACTGTTTGGGACCTCCGGTCAGAAAACCAAAATTAT AAGCAACAGAGGTGAAAACAGCTGCAAGGCCACAGGCCA GGTCTGCCATGCCTTGTGCTCCCCCGAGGGCTGCTGGGG CCCGGAGCCCAGGGACTGCGTCTCTTGCCGGAATGTCAG CCGAGGCAGGGAATGCGTGGACAAGTGCAACCTTCTGGA GGGTGAGCCAAGGGAGTTTGTGGAGAACTCTGAGTGCAT ACAGTGCCACCCAGAGTGCCTGCCTCAGGCCATGAACATC ACCTGCACAGGACGGGGACCAGACAACTGTATCCAGTGT GCCCACTACATTGACGGCCCCCACTGCGTCAAGACCTGCC CGGCAGGAGTCATGGGAGAAAACAACACCCTGGTCTGGA AGTACGCAGACGCCGGCCATGTGTGCCACCTGTGCCATCC AAACTGCACCTACGGATGCACTGGGCCAGGTC1IGAAGGC TGTCCAACGAATGGGCCTAAGATCCCGTCCATCGCCACTG GGATGGTGGGGGCCCTCCTCTTGCTGCTGGTGGTGGCCC TGGGGATCGGCCTCTTCATG | 34 |
| 39 | Signal peptide | MALPVTALLLPLALLLHAARP | 35 |
| 40 | scFv1 | DVVMTQTPLTLSVTIGQPASISCKSSQSLLDSDGKTNLNWL LQRPGQSPKRLIYLVSKLDSGVPDRFTGSGSGTDFTLKISRV EADDLGVYYCWQGTHFPWTFGGGTKLEIKGGGGSGGGGS GGGGSEVKLVESGPGLVAPSQSLTITCTVSGFSLTGYGVNW VRQPPGKGLEWLGMIWHNGSTDYNSALRSRLSINKDKSKN QVFLKMNSLQTDDTARYYCARGGRSPWFPYWGQGTLVTVS A | 36 |
| 41 | CD8 hinge | TTTPAPRPPTPAPTIASQPLSLRPEACRPAAGGAVHTRGLDFA C | 37 |
| 42 | CD28 Transmembrane intracellular | FWVLVVVGGVLACYSLLVTVAFIIFWVRSKRSRLLHSDYMN MTPRRPGPTRKHYQPYAPPRDFAAYRS | 38 |
| 43 | CD3 zeta | RVKFSRSADAPAYKQGQNQLYNELNLGRREEYDVLDKRRGR DPEMGGKPRRKNPQEGLYNELQKDKMAEAYSEIGMKGERR RGKGHDGLYQGLSTATKDTYDALHMQALPPR | 39 |
| 44 | T2A | EGRGSLLTCGDVEENPGP | 40 |
| 45 | EGFRt | MWLQSLLLLGTVACSISRKVCNGIGIGEFKDSLSINATNIKH FKNCTSISGDLHILPVAFRGDSFTHTPPLDPQELDILKTVKEI TGFLLIQAWPENRTDLHAFENLEIIRGRTKQHGQFSLAVVSL NITSLGLRSLKEISDGDVIISGNKNLCYANTINWKKLFGTSG QKTKIISNRGENSCKATGQVCHALCSPEGCWGPEPRDCVSC RNVSRGRECVDKCNLLEGEPREFVENSECIQCHPECLPQAM NITCTGRGPDNCIQCAHYIDGPHCVKTCPAGVMGENNTLVW KYADAGHVCHLCHPNCTYGCTGPGLEGCPTNGPKIPSIATG MVGALLLLLVVALGIGLFM | 41 |
| 46 | scFv2 | GATGTTGTGATGACCCAGACTCCACTCACTTTGTCGGTTAC CATTGGACAACCAGCCTCCATCTCTTGCAAGTCAAGTCAG AGCCTCTTAGATAGTGATGGAAAGACAAATTTGAATTGGT TGTTACAGAGGCCAGGCCAGTCTCCAAAGCGCCTAATCTA TCTGGTGTCTAAACTGGACTCTGGAGTCCCTGACAGGTTC ACTGGCAGTGGATCAGGGACAGATTTCACACTGAAAATCA | 42 |

TABLE 2-continued

Sequences of CAR construct

| No. | Name | Sequence | SEQ ID NO |
|---|---|---|---|
|  |  | GCAGAGTGGAGGCTGACGATTTGGGAGTTTATTATTGCTG GCAAGGTACACATTTTCCGTGGACGTTCGGTGGAGGCACC AAGCTGGAAATCAAAGGTGGAGGTGGCAGCGGAGGAGGT GGGTCCGGCGGTGGAGGAAGCGAGGTGAAGTTGGTGGA GTCAGGACCTGGCCTGGTGGCGCCCTCACAGAGCCTGAC CATCACATGCACCGTCTCAGGGTTCTCATTAACCGGCTAT GGTGTAAACTGGGTTCGCCAGCCTCCAGGAAAGGGTCTG GAGTGGCTGGGAATGATCTGGCATAATGGAAGCACAGAC TATAATTCAGCTCTCAGATCCAGACTGAGCATCAACAAGG ACAAGTCCAAGAACCAAGTTTTCTTAAAAATGAACAGTCTG CAAACTGATGACACAGCCAGGTACTACTGTGCCAGAGGG GGAAGGTCCCCCTGGTTTCCTTACTGGGGCCAAGGGACTC TGGTCACTGTCTCTGCAAGATCT |  |
| 47 | scFv2 | DVVMTQTPLTLSVTIGQPASISCKSSQSLLDSDGKT<u>YL</u>NWLL QRPGQSPKRLIYLVSKLDSGVPDRFTGSGSGTDFTL<u>KI</u>SRVE ADDLGVYYCWQGTHFPWTFGGGTKLEIKGGGGSGGGGSG GGGSEVKLVESGPGLVAPSQSLTITCTVSGFSLTGYGVNWV RQPPGKGLEWLGMIWHNGSTDYNSALRSRLSINKDKSKNQ VFLKMNSLQTDDTARYYCARGGRSPWFPYWGQGTLVTVSA | 43 |

Using GASP-1 granules as a CAR-T target, CAR-T therapy targeting cancer cell surface GASP-1 granules represents a new approach and would be effective against both hematologic and solid tumors.

Example 7. CAR-T Cells

Figure 12:
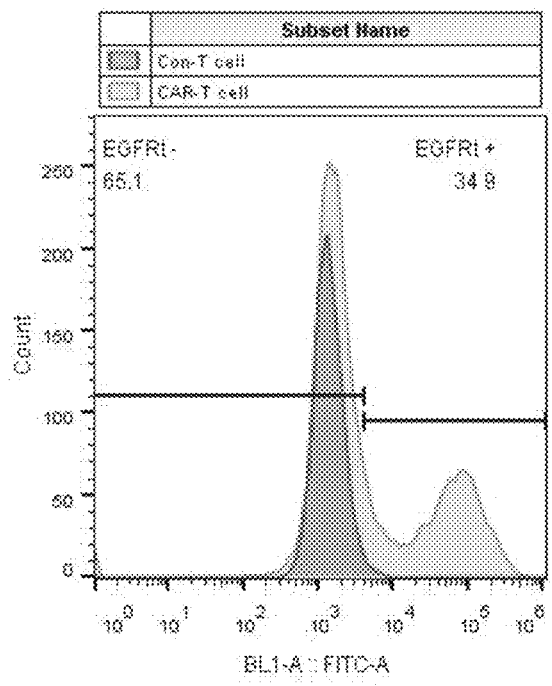
FIG. 12 shows 34.9% of the T cells are CAR-positive.

To assess CAR-T percentage, CAR-T cells were stained with Anti-EGFR and PE-conjugated Anti-human IgG. Flow cytometer analysis showed that 34.9% cells were CAR-positive (FIG. 12).

Figure 13:
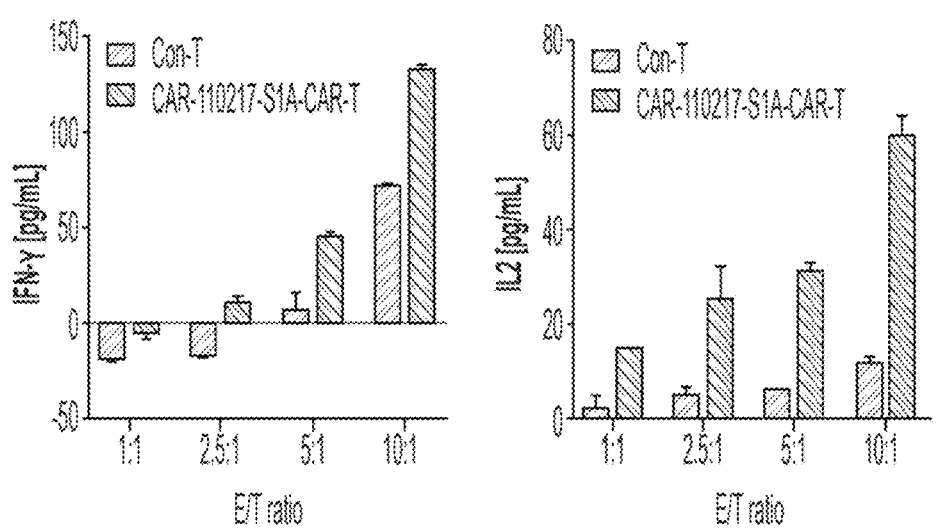
FIG. 13 shows release of IFN-γ (left panel) and IL-2 (right panel) by cancer cells upon exposure to CAR-10217-SIA-CAR-T cells.

To test the effectiveness of CAR-T, the CAR-T cells were co-cultured with target cell lines PC-3 at different E/T ratio for 24 hours, the supernatant was harvested for determination of cytokine release. The data showed that IL-2 and IFN-γ secreted by CAR-T cells were increased after being engaged with target tumor cells (FIG. 13).

Example 8. Construction of Humanized Antibodies Containing Anti-GASP-1 scFv Sequences A humanized antibody containing the scFv1 sequence was prepared. A first antibody may comprise amino acid sequences for a heavy chain (SEQ ID NO: 44), including a variable region VH (SEQ ID NO: 1) and a human constant region (SEQ ID NO: 45), and a light chain (SEQ ID: 46), including variable region VL1 (SEQ ID NO: 9) joined by a human constant region (SEQ ID NO: 47). A second antibody may comprise amino acid sequences for a heavy chain (SEQ ID NO: 44), including variable region VH (SEQ ID NO: 1) and a human constant region (SEQ ID NO: 45), and a light chain (SEQ ID: 48), including variable region VL2 (SEQ ID NO: 17) joined by a human constant region (SEQ ID NO: 47). Table 3 shows the various sequences used to make the anti-GASP-1 humanized antibodies. The designed chimeric antibody chains were synthesized and subcloned into the mammalian expression vector and were transiently transfected into HEK293 cells. The mAb was purified by Protein A affinity chromatography and SEC-HPLC. After ultrafiltration, the final product was subjected to 0.2-micron sterile filtration. The purity of the protein is >99% and the endotoxin is lower than 1 EU/mg.

TABLE 3

Humanized anti-GASP-1 antibody sequences

| No. | Name | Sequence | SEQ ID NO |
|---|---|---|---|
| 48 | Heavy Chain | EVKLVESGPGLVAPSQSLTITCTVSGFSLTGYGVNWVRQPPGKG LEWLGMIWHNGSTDYNSALRSRLSINKDKSKNQVFLKMNSLQT DDTARYYCARGGRSPWFPYWGQGTLVTVSAASTKGPSVFPLAPS SKSTSGGTAALGCLVKDYFPEPVTVSWNSGALTSGVHTFPAVLQ SSGLYSLSSVVTVPSSSLGTQTYICNVNHKPSNTKVDKKVEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSL SPGK | 44 |
| 49 | Human constant Heavy Chain | ASTKGPSVFPLAPSSKSTSGGTAALGCLVKDYFPEPVTVSWNSG ALTSGVHTFPAVLQSSGLYSLSSVVTVPSSSLGTQTYICNVNHKP SNTKVDKKVEPKSCDKTHTCPPCPAPELLGGPSVFLFPPKPKDTL MISRTPEVTCVVVDVSHEDPEVKFNWYVDGVEVHNAKTKPREEQ YNSTYRVVSVLTVLHQDWLNGKEYKCKVSNKALPAPIEKTISKAK | 45 |

TABLE 3-continued

Humanized anti-GASP-1 antibody sequences

| No. | Name | Sequence | SEQ ID NO |
|---|---|---|---|
| | | GQPREPQVYTLPPSRDELTKNQVSLTCLVKGFYPSDIAVEWESNG QPENNYKTTPPVLDSDGSFFLYSKLTVDKSRWQQGNVFSCSVM HEALHNHYTQKSLSLSPGK | |
| 50 | Light Chain 1 | DVVMTQTPLTLSVTIGQPASISCKSSQSLLDSDGKTNLNWLLQR PGQSPKRLIYLVSKLDSGVPDRFTGSGSGTDFTLKISRVEADDLG VYYCWQGTHFPWTFGGGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 46 |
| 51 | Human constant Light Chain | RTVAAPSVFIFPPSDEQLKSGTASVVCLLNNFYPREAKVQWKVDN ALQSGNSQESVTEQDSKDSTYSLSSILTLSKADYEKHKVYACEV THQGLSSPVTKSFNRGEC | 47 |
| 52 | Light Chain 2 | DVVMTQTPLTLSVTIGQPASISCKSSQSLLDSDGKTYLNWLLQRP GQSPKRLIYLVSKLDSGVPDRFTGSGSGTDFTLKISRVEADDLGV YYCWQGTHFPWTFGGGTKLEIKRTVAAPSVFIFPPSDEQLKSGTA SVVCLLNNFYPREAKVQWKVDNALQSGNSQESVTEQDSKDSTY SLSSTLTLSKADYEKHKVYACEVTHQGLSSPVTKSFNRGEC | 48 |

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method for detecting granules expressing G protein coupled receptor-associated sorting protein 1 (GASP-1) in cells, comprising:
   (a) contacting the cells with an effective amount of a binding protein, wherein the binding protein comprises an antigen binding fragment that specifically binds the GASP-1, wherein the binding protein comprises an anti-GASP-1 single-chain variable fragment (anti-GASP-1 scFv), whereby the binding protein is bound to the GASP-1, wherein the anti-GASP-1 scFv comprises a variable heavy (VH) chain and a variable light (VL) chain, and wherein the VH chain comprises an amino acid sequence of SEQ ID NO: 1 and the VL chain comprises SEQ ID NO: 9 or 17, or wherein the VH chain comprises the amino acid sequence of SEQ ID NO: 2, the amino acid sequence of SEQ ID NO: 3 and the amino acid sequence of SEQ ID NO: 4, and the VL chain comprises the amino acid sequence of SEQ ID NO: 10 or 18, the amino acid sequence of SEQ ID NO: 11, and the amino acid sequence of SEQ ID NO: 12; and
   (b) identifying the binding protein of step (a) in granules bound to a membrane of the cells, wherein the granules express the GASP-1 in the cells.

2. The method of claim 1, wherein the granules have a diameter in the range from 0.1 to 5.0 µm.

3. The method of claim 1, wherein the average number of the granules in the cells is in the range from 10 to 1,000 per cell.

4. The method of claim 1, wherein the granules are in the cytosol or on the surface of the cells.

5. The method of claim 1, wherein the cells are in a tumor.

6. The method of claim 5, wherein the tumor is a solid tumor or hematological tumor.

7. The method of claim 1, wherein the cells are cancer cells.

8. The method of claim 1, wherein the cells are in a subject having cancer.

9. The method of claim 8, wherein the cancer is selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma.

10. The method of claim 9, wherein the cancer is selected from the group consisting of bladder cancer, breast cancer, colon cancer, glioblastoma, liver cancer, lung cancer, melanoma, ovarian cancer, pancreatic cancer and prostate cancer.

11. The method of claim 9 or 10, wherein the breast cancer is high grade ductal carcinoma in situ (DCIS) breast cancer or triple negative breast cancer.

12. The method of claim 9 or 10, wherein the lung cancer is non-small cell lung cancer (NSCLC).

13. The method of claim 8, wherein the subject has received a cancer treatment.

14. The method of claim 1, further comprising detecting a cancer biomarker in the cells.

15. The method of claim 14, wherein the cancer biomarker is selected from the group consisting of CA125, CA19-9, CA15-3, CA27.29, AFP, BRCA1/BRCA2, EGFR, HER-2, KIT, VEGF, KRAS, ALK, PSA, HE4, CYFRA 21-1, NSE, PD-L1, TIMP-1, TIMP-2, HGF, OPN, MSLN, MMP2 and CEA.

16. The method of claim 1, wherein the binding protein is a humanized antibody.

17. The method of claim 1, wherein the VH chain comprises an amino acid sequence of SEQ ID NO: 1 and the VL chain comprises SEQ ID NO: 9.

18. The method of claim 1, wherein the VH chain comprises the amino acid sequence of SEQ ID NO: 2, the amino acid sequence of SEQ ID NO: 3, and the amino acid sequence of SEQ ID NO: 4, and the VL chain comprises the amino acid sequence of SEQ ID NO: 10, the amino acid sequence of SEQ ID NO: 11, and the amino acid sequence of SEQ ID NO: 12.

19. The method of claim 1, wherein the VH chain comprises an amino acid sequence of SEQ ID NO: 1 and the VL chain comprises SEQ ID NO: 17.

20. The method of claim 1, wherein the VH chain comprises the amino acid sequence of SEQ ID NO: 2, the amino acid sequence of SEQ ID NO: 3, and the amino acid sequence of SEQ ID NO: 4, and the VL chain comprises the amino acid sequence of SEQ ID NO: 18, the amino acid sequence of SEQ ID NO: 11, and the amino acid sequence of SEQ ID NO: 12.

21. The method of claim 1, wherein the VH chain is connected to the VL chain with a linker.

22. The method of claim 21 wherein the linker comprises the amino acid sequence of SEQ ID NO: 21.

23. The method of claim 1, wherein the GASP-1 comprises the amino acid sequence of SEQ ID NO: 22.

24. The method of claim 1, wherein the binding protein is an antibody selected from the group consisting of a recombinant monoclonal antibody, a polyclonal antibody, a humanized antibody and an antigen binding fragment thereof.

25. The method of claim 24, wherein the binding protein is a humanized antibody.

26. The method of claim 1, wherein the binding protein further comprises an amino acid sequence selected from the group consisting of SEQ ID NOs: 36 and 43.

27. The method of claim 1, wherein the binding protein is conjugated with a chemotherapeutic agent.

28. The method of claim 27, wherein the chemotherapeutic agent is selected from the group consisting of Anastrozole, Exemestane, Letrozole, Palbociclib, Ribociclib, Neratinib, Abemaciclib, Olaparib, Regorafenib, Tretinoin, axicabtagene ciloleucel, Dasatinib, Nilotinib, Bosutinib, Ibrutinib, Idelalisib, Venetoclax, Ponatinib, Midostaurin, Enasidenib, Tisagenlecleucel, Ivosideni, Duvelisib, Imatinib, Gefitinib, Erlotinib, Lapatinib, Sorafenib, Abiraterone, Critozinib, Vemurafenib, radioactive isotopes, toxins, maytansinoids, doxorubicin, taxols, cisplatin, vinblastine, calicheamicin, and *Pseudomonas* exotoxin A.

29. The method of claim 1, wherein the cells are from a subject having a GASP-1-mediated disease or disorder, further comprising administering the binding protein to the subject in an effective amount for treating the GASP-1-mediated disease or disorder in the subject.

30. The method of claim 29, wherein the GASP-1-mediated disease or disorder is a tumor.

31. The method of claim 30, wherein the tumor is a solid tumor.

32. The method of claim 30, wherein the tumor is a hematological tumor.

33. The method of claim 29, wherein the GASP-1-mediated disease or disorder is cancer.

34. The method of claim 29, wherein the subject has received a treatment of cancer.

35. The method of claim 29, wherein the granules are in the cytosol or on the surface of the cells.

36. The method of claim 1, further comprising administering the binding protein to the cells in an effective amount for inhibiting growth of the cells.

37. The method of claim 36, wherein the cells are cancer cells.

38. The method of claim 36, wherein the cells are in a patient having cancer.

39. The method of claim 1, further comprising inactivating exosomes, microvesicles, or oncosomes expressing GASP-1.

40. The method of claim 39, wherein the exosomes, microvesicles, or oncosomes are in a subject having cancer.

41. The method of claim 40, wherein the exosomes, microvesicles, or oncosomes are in blood circulation of the subject.

42. The method of claim 33, wherein the cancer is selected from the group consisting of bladder cancer, breast cancer, colon cancer, endometrial carcinoma, esophagus squamous cell carcinoma, glioma, head cancer, hepatocellular carcinoma, infiltrating ductal breast carcinoma, larynx cancer, lung cancer, melanoma, mucinous cystadenocarcinoma of ovary, neck cancer, ovarian cancer, pancreatic cancer, prostate cancer, renal cell carcinoma, small bowel malignant stromal tumor and stomach adenocarcinoma.

43. The method of claim 33, wherein the cancer is selected from the group consisting of bladder cancer, breast cancer, colon cancer, glioblastoma, liver cancer, lung cancer, melanoma, ovarian cancer, pancreatic cancer and prostate cancer.

44. The method of claim 42 or 43, wherein the breast cancer is high grade ductal carcinoma in situ (DCIS) breast cancer or triple negative breast cancer.

45. The method of claim 42 or 43, wherein the lung cancer is non-small cell lung cancer (NSCLC).

* * * * *

SEQUENCE LISTING

<160> NUMBER OF SEQ ID NOS: 48

<210> SEQ ID NO 1
<211> LENGTH: 117
<212> TYPE: PRT
<213> ORGANISM: Mus musculus

<400> SEQUENCE: 1

Glu Val Lys Leu Val Glu Ser Gly Pro Gly Leu Val Ala Pro Ser Gln
1               5                   10                  15

Ser Leu Thr Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp His Asn Gly Ser Thr Asp Tyr Asn Ser Ala Leu Arg
    50                  55                  60

Ser Arg Leu Ser Ile Asn Lys Asp Lys Ser Lys Asn Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Arg Ser Pro Trp Phe Pro Tyr Trp Gly Gln Gly Thr Leu
            100                 105                 110

Val Thr Val Ser Ala
        115

<210> SEQ ID NO 2
<211> LENGTH: 7
<212> TYPE: PRT
<213> ORGANISM: Mus musculus

<400> SEQUENCE: 2

Gly Phe Ser Leu Thr Gly Tyr
1               5

```
<210> SEQ ID NO 3
<211> LENGTH: 5
<212> TYPE: PRT
<213> ORGANISM: Mus musculus

<400> SEQUENCE: 3

Trp His Asn Gly Ser
1               5

<210> SEQ ID NO 4
<211> LENGTH: 9
<212> TYPE: PRT
<213> ORGANISM: Mus musculus

<400> SEQUENCE: 4

Gly Gly Arg Ser Pro Trp Phe Pro Tyr
1               5

<210> SEQ ID NO 5
<211> LENGTH: 351
<212> TYPE: DNA
<213> ORGANISM: Mus musculus

<400> SEQUENCE: 5
gaggtgaagt tggtggagtc aggacctggc ctggtggcgc cctcacagag cctgaccatc      60
acatgcaccg tctcagggtt ctcattaacc ggctatggtg taaactgggt tcgccagcct     120
ccaggaaagg gtctggagtg gctgggaatg atctggcata atggaagcac agactataat     180
tcagctctca gatccagact gagcatcaac aaggacaagt ccaagaacca agttttctta     240
aaaatgaaca gtctgcaaac tgatgacaca gccaggtact actgtgccag agggggaagg     300 tcccccctggt tccttactg gggccaaggg actctggtca ctgtctctgc a              351

<210> SEQ ID NO 6
<211> LENGTH: 21
<212> TYPE: DNA
<213> ORGANISM: Mus musculus

<400> SEQUENCE: 6
gggttctcat taaccggcta t                                                21

<210> SEQ ID NO 7
<211> LENGTH: 15
<212> TYPE: DNA
<213> ORGANISM: Mus musculus

<400> SEQUENCE: 7
tggcataatg gaagc                                                       15

<210> SEQ ID NO 8
<211> LENGTH: 27
<212> TYPE: DNA
<213> ORGANISM: Mus musculus

<400> SEQUENCE: 8
gggggaaggt ccccctggtt tccttac                                          27

<210> SEQ ID NO 9
<211> LENGTH: 112
<212> TYPE: PRT
<213> ORGANISM: Mus musculus

<400> SEQUENCE: 9
```

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Asn Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65              70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
                100                 105                 110

<210> SEQ ID NO 10
<211> LENGTH: 16
<212> TYPE: PRT
<213> ORGANISM: Mus musculus

<400> SEQUENCE: 10

Lys Ser Ser Gln Ser Leu Leu Asp Ser Asp Gly Lys Thr Asn Leu Asn
1               5                   10                  15

<210> SEQ ID NO 11
<211> LENGTH: 7
<212> TYPE: PRT
<213> ORGANISM: Mus musculus

<400> SEQUENCE: 11

Leu Val Ser Lys Leu Asp Ser
1               5

<210> SEQ ID NO 12
<211> LENGTH: 9
<212> TYPE: PRT
<213> ORGANISM: Mus musculus

<400> SEQUENCE: 12

Trp Gln Gly Thr His Phe Pro Trp Thr
1               5

<210> SEQ ID NO 13
<211> LENGTH: 336
<212> TYPE: DNA
<213> ORGANISM: Mus musculus

<400> SEQUENCE: 13
gatgttgtga tgacccagac tccactcact ttgtcggtta ccattggaca accagcctcc    60
atctcttgca agtcaagtca gagcctctta gatagtgatg gaaagacata tttgaattgg   120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgacga tttgggagtt tattattgct ggcaaggtac acattttccg   300
tggacgttcg gtggaggcac caagctggaa atcaaa                             336

<210> SEQ ID NO 14
<211> LENGTH: 48
<212> TYPE: DNA

<213> ORGANISM: Mus musculus

<400> SEQUENCE: 14
aagtcaagtc agagcctctt agatagtgat ggaaagacat atttgaat         48

<210> SEQ ID NO 15
<211> LENGTH: 21
<212> TYPE: DNA
<213> ORGANISM: Mus musculus

<400> SEQUENCE: 15
ctggtgtcta aactggactc t         21

<210> SEQ ID NO 16
<211> LENGTH: 27
<212> TYPE: DNA
<213> ORGANISM: Mus musculus

<400> SEQUENCE: 16
tggcaaggta cacattttcc gtggacg         27

<210> SEQ ID NO 17
<211> LENGTH: 112
<212> TYPE: PRT
<213> ORGANISM: Mus musculus

<400> SEQUENCE: 17

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 18
<211> LENGTH: 16
<212> TYPE: PRT
<213> ORGANISM: Mus musculus

<400> SEQUENCE: 18

Lys Ser Ser Gln Ser Leu Leu Asp Ser Asp Gly Lys Thr Tyr Leu Asn
1               5                   10                  15

<210> SEQ ID NO 19
<211> LENGTH: 336
<212> TYPE: DNA
<213> ORGANISM: Mus musculus

<400> SEQUENCE: 19
gatgttgtga tgacccagac tccactcact ttgtcggtta ccattggaca accagcctcc         60
atctcttgca agtcaagtca gagcctctta gatagtgatg gaaagacaaa tttgaattgg        120
ttgttacaga ggccaggcca gtctccaaag cgcctaatct atctggtgtc taaactggac        180

```
tctggagtcc ctgacaggtt cactggcagt ggatcaggga cagatttcac actgaaaatc    240
agcagagtgg aggctgacga tttgggagtt tattattgct ggcaaggtac acattttccg    300
tggacgttcg gtggaggcac caagctggaa atcaaa                              336
```

<210> SEQ ID NO 20
<211> LENGTH: 48
<212> TYPE: DNA
<213> ORGANISM: Mus musculus

<400> SEQUENCE: 20

```
aagtcaagtc agagcctctt agatagtgat ggaaagacaa atttgaat                  48
```

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

```
Gly Gly Gly Gly Ser Gly Gly Gly Gly Ser Gly Gly Gly Gly
1               5                   10
```

<210> SEQ ID NO 22
<211> LENGTH: 16
<212> TYPE: PRT
<213> ORGANISM: Homo sapiens

<400> SEQUENCE: 22

```
Glu Glu Ala Ser Pro Glu Ala Val Ala Gly Val Gly Phe Glu Ser Lys
1               5                   10                  15
```

<210> SEQ ID NO 23
<211> LENGTH: 13
<212> TYPE: PRT
<213> ORGANISM: Artificial Sequence
<220> FEATURE:
<223> OTHER INFORMATION: Synthetic

<400> SEQUENCE: 23

```
Trp Lys Glu Asp Glu Ala Ile Ser Glu Ala Thr Asp Arg
1               5                   10
```

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

```
Cys Ser Lys Ser Ser Pro Lys Ala Glu Glu Glu Glu Val
1               5                   10
```

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

```
Glu Glu Ala Ser Ile Gln Ala Gly Ser Gln Ala Val Glu Glu
1               5                   10
```

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Phe Trp Asp Gly Lys Glu Val Ser Glu Glu Ala Gly Pro Cys
1               5                   10

<210> SEQ ID NO 27
<211> LENGTH: 1335
<212> TYPE: DNA
<213> ORGANISM: Artificial Sequence
<220> FEATURE:
<223> OTHER INFORMATION: Synthetic

<400> SEQUENCE: 27

```
gagtaattca tacaaaagga ctcgcccctg ccttggggaa tcccagggac cgtcgttaaa      60
ctcccactaa cgtagaaccc agagatcgct gcgttcccgc cccctcaccc gcccgctctc     120
gtcatcactg aggtggagaa gagcatgcgt gaggctccgg tgcccgtcag tgggcagagc     180
gcacatcgcc cacagtcccc gagaagttgg ggggaggggt cggcaattga accggtgcct     240
agagaaggtg gcgcggggta aactgggaaa gtgatgtcgt gtactggctc cgcctttttc     300
ccgagggtgg gggagaaccg tatataagtg cagtagtcgc cgtgaacgtt cttttttcgca    360 acgggtttgc cgccagaaca caggtaagtg ccgtgtgtgg ttcccgcggg cctggcctct     420
ttacgggtta tggcccttgc gtgccttgaa ttacttccac gcccctggct gcagtacgtg     480
attcttgatc ccgagcttcg ggttggaagt gggtgggaga gttcgaggcc ttgcgcttaa     540 ggagccccctt cgcctcgtgc ttgagttgag gcctggcttg ggcgctgggg ccgccgcgtg    600
cgaatctggt ggcaccttcg cgcctgtctc gctgctttcg ataagtctct agccatttaa    660 aattttgat gacctgctgc gacgcttttt ttctggcaag atagtcttgt aaatgcgggc      720
caagatctgc acactggtat ttcggttttt ggggccgcgg gcggcgacgg ggcccgtgcg     780
tcccagcgca catgttcggc gaggcgggc ctgcgagcgc ggccaccgag aatcggacgg      840
gggtagtctc aagctggccg gcctgctctg gtgcctggcc tcgcgccgcc gtgtatcgcc     900
ccgccctggg cggcaaggct ggcccggtcg gcaccagttg cgtgagcgga agatggccg      960 cttcccggcc ctgctgcagg gagctcaaaa tggaggacgc ggcgctcggg agagcgggcg    1020
ggtgagtcac ccacacaaag gaaaagggcc tttccgtcct cagccgtcgc ttcatgtgac    1080
tccacggagt accgggcgcc gtccaggcac ctcgattagt tctcgagctt ttggagtacg    1140
tcgtctttag gttgggggga ggggttttat gcgatggagt ttccccacac tgagtgggtg    1200
gagactgaag ttaggccagc ttggcacttg atgtaattct ccttggaatt tgccctttt     1260 gagtttggat cttggttcat tctcaagcct cagacagtgg ttcaaagttt ttttcttcca    1320
tttcaggtgt cgtga                                                    1335
```

<210> SEQ ID NO 28
<211> LENGTH: 63
<212> TYPE: DNA
<213> ORGANISM: Artificial Sequence
<220> FEATURE:
<223> OTHER INFORMATION: Synthetic

<400> SEQUENCE: 28

```
atggccttac cagtgaccgc cttgctcctg ccgctggcct tgctgctcca cgccgccagg    60
ccg                                                                  63
```

<210> SEQ ID NO 29
<211> LENGTH: 738
<212> TYPE: PRT
<213> ORGANISM: Artificial Sequence
<220> FEATURE:
<223> OTHER INFORMATION: Synthetic

<400> SEQUENCE: 29

```
Gly Ala Thr Gly Thr Gly Thr Gly Ala Thr Gly Ala Cys Cys Cys
1               5                   10                  15

Ala Gly Ala Cys Thr Cys Cys Ala Cys Thr Cys Ala Cys Thr Thr Thr
            20                  25                  30

Gly Thr Cys Gly Gly Thr Thr Ala Cys Ala Thr Gly Gly Ala
        35                  40                  45

Cys Ala Ala Cys Cys Ala Gly Cys Cys Thr Cys Ala Thr Cys Thr
50                  55                  60

Cys Thr Thr Gly Cys Ala Ala Gly Thr Cys Ala Ala Gly Thr Cys Ala
65                  70                  75                  80

Gly Ala Gly Cys Cys Thr Cys Thr Thr Ala Gly Ala Thr Ala Gly Thr
                85                  90                  95

Gly Ala Thr Gly Gly Ala Ala Gly Ala Cys Ala Thr Ala Thr Thr
            100                 105                 110

Thr Gly Ala Ala Thr Thr Gly Gly Thr Thr Gly Thr Thr Ala Cys Ala
        115                 120                 125

Gly Ala Gly Gly Cys Cys Ala Gly Gly Cys Cys Ala Gly Thr Cys Thr
130                 135                 140

Cys Cys Ala Ala Ala Gly Cys Gly Cys Cys Thr Ala Ala Thr Cys Thr
145                 150                 155                 160

Ala Thr Cys Thr Gly Gly Thr Gly Thr Cys Thr Ala Ala Ala Cys Thr
                165                 170                 175

Gly Gly Ala Cys Thr Cys Thr Gly Gly Ala Gly Thr Cys Cys Cys Thr
            180                 185                 190

Gly Ala Cys Ala Gly Gly Thr Thr Cys Ala Cys Thr Gly Gly Cys Ala
        195                 200                 205

Gly Thr Gly Gly Ala Thr Cys Ala Gly Gly Ala Cys Ala Gly Ala
            210                 215                 220

Thr Thr Thr Cys Ala Cys Ala Cys Thr Gly Ala Ala Ala Ala Thr Cys
225                 230                 235                 240

Ala Gly Cys Ala Gly Ala Gly Thr Gly Gly Ala Gly Gly Cys Thr Gly
                245                 250                 255

Ala Cys Gly Ala Thr Thr Thr Gly Gly Gly Ala Gly Thr Thr Thr Ala
            260                 265                 270

Thr Thr Ala Thr Thr Gly Cys Thr Gly Gly Cys Ala Ala Gly Gly Thr
        275                 280                 285

Ala Cys Ala Cys Ala Thr Thr Thr Thr Cys Cys Gly Thr Gly Gly Ala
    290                 295                 300

Cys Gly Thr Thr Cys Gly Gly Thr Gly Gly Gly Gly Cys Ala Cys
305                 310                 315                 320

Cys Ala Ala Gly Cys Thr Gly Gly Ala Ala Thr Cys Ala Ala Ala
                325                 330                 335

Gly Gly Thr Gly Gly Ala Gly Gly Thr Gly Gly Cys Ala Gly Cys Gly
```

```
              340                 345                 350
Gly Ala Gly Gly Ala Gly Thr Gly Gly Thr Cys Cys Gly Gly
            355                 360                 365
Cys Gly Gly Thr Gly Ala Gly Gly Ala Ala Gly Cys Gly Ala Gly
            370                 375                 380
Gly Thr Gly Ala Ala Gly Thr Thr Gly Gly Thr Gly Gly Ala Gly Thr
385                 390                 395                 400
Cys Ala Gly Gly Ala Cys Cys Thr Gly Gly Cys Cys Thr Gly Thr
            405                 410                 415
Gly Gly Cys Gly Cys Cys Thr Cys Ala Cys Ala Gly Ala Gly Cys
            420                 425                 430
Cys Thr Gly Ala Cys Cys Ala Thr Cys Ala Cys Ala Thr Gly Cys Ala
            435                 440                 445
Cys Cys Gly Thr Cys Thr Cys Ala Gly Gly Thr Thr Cys Thr Cys
            450                 455                 460
Ala Thr Thr Ala Ala Cys Cys Gly Gly Cys Thr Ala Thr Gly Gly Thr
465                 470                 475                 480
Gly Thr Ala Ala Ala Cys Thr Gly Gly Thr Thr Cys Gly Cys Cys
            485                 490                 495
Ala Gly Cys Cys Thr Cys Cys Ala Gly Gly Ala Ala Gly Gly Gly
            500                 505                 510
Thr Cys Thr Gly Gly Ala Gly Thr Gly Gly Cys Thr Gly Gly Gly Ala
            515                 520                 525
Ala Thr Gly Ala Thr Cys Thr Gly Gly Cys Ala Thr Ala Ala Thr Gly
            530                 535                 540
Gly Ala Ala Gly Cys Ala Cys Ala Gly Ala Cys Thr Ala Thr Ala Ala
545                 550                 555                 560
Thr Thr Cys Ala Gly Cys Thr Cys Thr Cys Ala Gly Ala Thr Cys Cys
            565                 570                 575
Ala Gly Ala Cys Thr Gly Ala Gly Cys Ala Thr Cys Ala Ala Cys Ala
            580                 585                 590
Ala Gly Gly Ala Cys Ala Ala Gly Thr Cys Cys Ala Ala Gly Ala Ala
            595                 600                 605
Cys Cys Ala Ala Gly Thr Thr Thr Cys Thr Ala Ala Ala Ala
            610                 615                 620
Ala Thr Gly Ala Ala Cys Ala Gly Thr Cys Thr Gly Cys Ala Ala Ala
625                 630                 635                 640
Cys Thr Gly Ala Thr Gly Ala Cys Ala Cys Ala Gly Cys Cys Ala Gly
            645                 650                 655
Gly Thr Ala Cys Thr Ala Cys Thr Gly Thr Gly Cys Cys Ala Gly Ala
            660                 665                 670
Gly Gly Gly Gly Ala Ala Gly Thr Cys Cys Cys Cys Thr
            675                 680                 685
Gly Gly Thr Thr Thr Cys Cys Thr Thr Ala Cys Thr Gly Gly Gly Gly
            690                 695                 700
Cys Cys Ala Ala Gly Gly Gly Ala Cys Thr Cys Thr Gly Gly Thr Cys
705                 710                 715                 720
Ala Cys Thr Gly Thr Cys Thr Cys Thr Gly Cys Ala Ala Gly Ala Thr
            725                 730                 735

Cys Thr

<210> SEQ ID NO 30
<211> LENGTH: 135
```

```
<212> TYPE: PRT
<213> ORGANISM: Artificial Sequence
<220> FEATURE:
<223> OTHER INFORMATION: Synthetic

<400> SEQUENCE: 30

Cys Cys Ala Cys Gly Ala Cys Gly Cys Ala Gly Cys Gly Cys Cys
1               5                   10                  15

Gly Cys Gly Ala Cys Cys Ala Cys Cys Ala Ala Cys Ala Cys Cys Gly
            20                  25                  30

Gly Cys Gly Cys Cys Ala Cys Cys Ala Thr Cys Gly Cys Gly Thr
        35                  40                  45

Cys Gly Cys Ala Gly Cys Cys Cys Thr Gly Thr Cys Cys Cys Thr
    50                  55                  60

Gly Cys Gly Cys Cys Cys Ala Gly Ala Gly Gly Cys Gly Thr Gly Cys
65                  70                  75                  80

Cys Gly Gly Cys Cys Ala Gly Cys Gly Gly Cys Gly Gly Gly Gly
            85                  90                  95

Gly Cys Gly Cys Ala Gly Thr Gly Cys Ala Cys Ala Cys Gly Ala Gly
            100                 105                 110

Gly Gly Gly Gly Cys Thr Gly Gly Ala Cys Thr Thr Cys Gly Cys Cys
        115                 120                 125

Thr Gly Thr Gly Ala Thr Ala
    130                 135

<210> SEQ ID NO 31
<211> LENGTH: 204
<212> TYPE: DNA
<213> ORGANISM: Artificial Sequence
<220> FEATURE:
<223> OTHER INFORMATION: Synthetic

<400> SEQUENCE: 31
ttctgggtgc tggtcgttgt gggcggcgtg ctggcctgct acagcctgct ggtgacagtg      60
gccttcatca tcttttgggt gaggagcaag cggagcagac tgctgcacag cgactacatg     120
aacatgaccc ccggaggcc tggccccacc cggaagcact accagcccta cgcccctccc      180
agggatttcg ccgcctaccg gagc                                            204

<210> SEQ ID NO 32
<211> LENGTH: 336
<212> TYPE: DNA
<213> ORGANISM: Artificial Sequence
<220> FEATURE:
<223> OTHER INFORMATION: Synthetic

<400> SEQUENCE: 32
agagtgaagt tcagcaggag cgcagacgcc cccgcgtaca gcagggcca gaaccagctc       60 tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga aagataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcgc                              336

<210> SEQ ID NO 33
<211> LENGTH: 54
<212> TYPE: DNA
<213> ORGANISM: Artificial Sequence
```

<220> FEATURE:
<223> OTHER INFORMATION: Synthetic

<400> SEQUENCE: 33

```
gagggcagag gcagcctgct gacatggtggc gacgtggaag agaaccctgg cccc        54
```

<210> SEQ ID NO 34
<211> LENGTH: 1056
<212> TYPE: DNA
<213> ORGANISM: Artificial Sequence
<220> FEATURE:
<223> OTHER INFORMATION: Synthetic

<400> SEQUENCE: 34

```
atgtggctgc agagcctgct gctcttgggc actgtggcct gcagcatctc tcgcaaagtg        60
tgtaacggaa taggtattgg tgaatttaaa gactcactct ccataaatgc tacgaatatt      120
aaacacttca aaactgcac ctccatcagt ggcgatctcc acatcctgcc ggtggcattt      180
agggtgact ccttcacaca tactcctcct ctggatccac aggaactgga tattctgaaa      240
accgtaaagg aaatcacagg ttttttgctg attcaggctt ggcctgaaaa caggacggac      300
ctccatgcct ttgagaacct agaaatcata cgcggcagga ccaagcaaca tggtcagttt      360
tctcttgcag tcgtcagcct gaacataaca tccttgggat tacgctccct caaggagata      420
agtgatggag atgtgataat ttcaggaaac aaaaatttgt gctatgcaaa tacaataaac      480
tggaaaaaac tgtttgggac ctccggtcag aaaaccaaaa ttataagcaa cagaggtgaa      540
aacagctgca aggccacagg ccaggtctgc catgccttgt gctcccccga gggctgctgg      600
ggcccggagc ccagggactg cgtctcttgc cggaatgtca gccgaggcag ggaatgcgtg      660
gacaagtgca accttctgga gggtgagcca agggagtttg tggagaactc tgagtgcata      720
cagtgccacc cagagtgcct gcctcaggcc atgaacatca cctgcacagg acggggacca      780
gacaactgta tccagtgtgc ccactacatt gacggccccc actgcgtcaa gacctgcccg      840
gcaggagtca tgggagaaaa caacaccctg gtctggaagt acgcagacgc cggccatgtg      900
tgccacctgt gccatccaaa ctgcacctac ggatgcactg gccaggtct tgaaggctgt      960
ccaacgaatg ggcctaagat cccgtccatc gccactggga tggtggggc cctcctcttg     1020
ctgctggtgg tggccctggg gatcggcctc ttcatg                              1056
```

<210> SEQ ID NO 35
<211> LENGTH: 21
<212> TYPE: PRT
<213> ORGANISM: Artificial Sequence
<220> FEATURE:
<223> OTHER INFORMATION: Synthetic

<400> SEQUENCE: 35

```
Met Ala Leu Pro Val Thr Ala Leu Leu Pro Leu Ala Leu Leu Leu
1               5                   10                  15

His Ala Ala Arg Pro
            20
```

<210> SEQ ID NO 36
<211> LENGTH: 244
<212> TYPE: PRT
<213> ORGANISM: Artificial Sequence
<220> FEATURE:
<223> OTHER INFORMATION: Synthetic

<400> SEQUENCE: 36

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Asn Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Gly Gly Gly Gly Ser Gly Gly Gly Gly Ser Gly Gly Gly Gly Ser Glu
            115                 120                 125

Val Lys Leu Val Glu Ser Gly Pro Gly Leu Val Ala Pro Ser Gln Ser
        130                 135                 140

Leu Thr Ile Thr Cys Thr Val Ser Gly Phe Ser Leu Thr Gly Tyr Gly
145                 150                 155                 160

Val Asn Trp Val Arg Gln Pro Pro Gly Lys Gly Leu Glu Trp Leu Gly
                165                 170                 175

Met Ile Trp His Asn Gly Ser Thr Asp Tyr Asn Ser Ala Leu Arg Ser
            180                 185                 190

Arg Leu Ser Ile Asn Lys Asp Lys Ser Lys Asn Gln Val Phe Leu Lys
        195                 200                 205

Met Asn Ser Leu Gln Thr Asp Asp Thr Ala Arg Tyr Tyr Cys Ala Arg
210                 215                 220

Gly Gly Arg Ser Pro Trp Phe Pro Tyr Trp Gly Gln Gly Thr Leu Val
225                 230                 235                 240

Thr Val Ser Ala

<210> SEQ ID NO 37
<211> LENGTH: 44
<212> TYPE: PRT
<213> ORGANISM: Artificial Sequence
<220> FEATURE:
<223> OTHER INFORMATION: Synthetic

<400> SEQUENCE: 37

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys
        35                  40

<210> SEQ ID NO 38
<211> LENGTH: 68
<212> TYPE: PRT
<213> ORGANISM: Artificial Sequence
<220> FEATURE:
<223> OTHER INFORMATION: Synthetic

<400> SEQUENCE: 38

Phe Trp Val Leu Val Val Val Gly Gly Val Leu Ala Cys Tyr Ser Leu
1               5                   10                  15
```

```
Leu Val Thr Val Ala Phe Ile Ile Phe Trp Val Arg Ser Lys Arg Ser
                20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65

<210> SEQ ID NO 39
<211> LENGTH: 112
<212> TYPE: PRT
<213> ORGANISM: Artificial Sequence
<220> FEATURE:
<223> OTHER INFORMATION: Synthetic

<400> SEQUENCE: 39

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Glu Gly Arg Gly Ser Leu Leu Thr Cys Gly Asp Val Glu Glu Asn Pro
1               5                   10                  15

Gly Pro

<210> SEQ ID NO 41
<211> LENGTH: 352
<212> TYPE: PRT
<213> ORGANISM: Artificial Sequence
<220> FEATURE:
<223> OTHER INFORMATION: Synthetic

<400> SEQUENCE: 41

Met Trp Leu Gln Ser Leu Leu Leu Leu Gly Thr Val Ala Cys Ser Ile
1               5                   10                  15

Ser Arg Lys Val Cys Asn Gly Ile Gly Ile Gly Glu Phe Lys Asp Ser
                20                  25                  30

Leu Ser Ile Asn Ala Thr Asn Ile Lys His Phe Lys Asn Cys Thr Ser
            35                  40                  45

Ile Ser Gly Asp Leu His Ile Leu Pro Val Ala Phe Arg Gly Asp Ser
        50                  55                  60
```

Phe Thr His Thr Pro Pro Leu Asp Pro Gln Glu Leu Asp Ile Leu Lys
65                  70                  75                  80

Thr Val Lys Glu Ile Thr Gly Phe Leu Leu Ile Gln Ala Trp Pro Glu
            85                  90                  95

Asn Arg Thr Asp Leu His Ala Phe Glu Asn Leu Glu Ile Ile Arg Gly
                100                 105                 110

Arg Thr Lys Gln His Gly Gln Phe Ser Leu Ala Val Val Ser Leu Asn
            115                 120                 125

Ile Thr Ser Leu Gly Leu Arg Ser Leu Lys Glu Ile Ser Asp Gly Asp
130                 135                 140

Val Ile Ile Ser Gly Asn Lys Asn Leu Cys Tyr Ala Asn Thr Ile Asn
145                 150                 155                 160

Trp Lys Lys Leu Phe Gly Thr Ser Gly Gln Lys Thr Lys Ile Ile Ser
                165                 170                 175

Asn Arg Gly Glu Asn Ser Cys Lys Ala Thr Gly Gln Val Cys His Ala
                180                 185                 190

Leu Cys Ser Pro Glu Gly Cys Trp Gly Pro Glu Pro Arg Asp Cys Val
            195                 200                 205

Ser Cys Arg Asn Val Ser Arg Gly Arg Glu Cys Val Asp Lys Cys Asn
210                 215                 220

Leu Leu Glu Gly Glu Pro Arg Glu Phe Val Glu Asn Ser Glu Cys Ile
225                 230                 235                 240

Gln Cys His Pro Glu Cys Leu Pro Gln Ala Met Asn Ile Thr Cys Thr
            245                 250                 255

Gly Arg Gly Pro Asp Asn Cys Ile Gln Cys Ala His Tyr Ile Asp Gly
            260                 265                 270

Pro His Cys Val Lys Thr Cys Pro Ala Gly Val Met Gly Glu Asn Asn
            275                 280                 285

Thr Leu Val Trp Lys Tyr Ala Asp Ala Gly His Val Cys His Leu Cys
290                 295                 300

His Pro Asn Cys Thr Tyr Gly Cys Thr Gly Pro Gly Leu Glu Gly Cys
305                 310                 315                 320

Pro Thr Asn Gly Pro Lys Ile Pro Ser Ile Ala Thr Gly Met Val Gly
            325                 330                 335

Ala Leu Leu Leu Leu Leu Val Val Ala Leu Gly Ile Gly Leu Phe Met
            340                 345                 350

<210> SEQ ID NO 42
<211> LENGTH: 738
<212> TYPE: DNA
<213> ORGANISM: Artificial Sequence
<220> FEATURE:
<223> OTHER INFORMATION: Synthetic

<400> SEQUENCE: 42
gatgttgtga tgacccagac tccactcact ttgtcggtta ccattggaca accagcctcc      60
atctcttgca agtcaagtca gagcctctta gatagtgatg aaagacaaa tttgaattgg      120 ttgttacaga ggccaggcca gtctccaaag cgcctaatct atctggtgtc taaactggac     180
tctggagtcc ctgacaggtt cactggcagt ggatcaggga cagatttcac actgaaaatc    240
agcagagtgg aggctgacga tttgggagtt tattattgct ggcaaggtac acattttccg    300
tggacgttcg gtgaggcac caagctggaa atcaaaggtg gaggtggcag cggaggaggt    360
gggtccggcg gtggaggaag cgaggtgaag ttggtggagt caggacctgg cctggtggcg    420

```
ccctcacaga gcctgaccat acacatgcacc gtctcagggt tctcattaac cggctatggt    480
gtaaactggg ttcgccagcc tccaggaaag ggtctggagt ggctgggaat gatctggcat    540
aatggaagca cagactataa ttcagctctc agatccagac tgagcatcaa caaggacaag    600
tccaagaacc aagttttctt aaaaatgaac agtctgcaaa ctgatgacac agccaggtac    660
tactgtgcca gaggggggaag gtcccccctgg tttccttact ggggccaagg gactctggtc    720
actgtctctg caagatct                                                   738
```

<210> SEQ ID NO 43
<211> LENGTH: 244
<212> TYPE: PRT
<213> ORGANISM: Artificial Sequence
<220> FEATURE:
<223> OTHER INFORMATION: Synthetic

<400> SEQUENCE: 43

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Gly Gly Gly Gly Ser Gly Gly Gly Ser Gly Gly Gly Ser Glu
        115                 120                 125

Val Lys Leu Val Glu Ser Gly Pro Gly Leu Val Ala Pro Ser Gln Ser
    130                 135                 140

Leu Thr Ile Thr Cys Thr Val Ser Gly Phe Ser Leu Thr Gly Tyr Gly
145                 150                 155                 160

Val Asn Trp Val Arg Gln Pro Pro Gly Lys Gly Leu Glu Trp Leu Gly
                165                 170                 175

Met Ile Trp His Asn Gly Ser Thr Asp Tyr Asn Ser Ala Leu Arg Ser
            180                 185                 190

Arg Leu Ser Ile Asn Lys Asp Lys Ser Lys Asn Gln Val Phe Leu Lys
        195                 200                 205

Met Asn Ser Leu Gln Thr Asp Asp Thr Ala Arg Tyr Tyr Cys Ala Arg
    210                 215                 220

Gly Gly Arg Ser Pro Trp Phe Pro Tyr Trp Gly Gln Gly Thr Leu Val
225                 230                 235                 240

Thr Val Ser Ala
```

<210> SEQ ID NO 44
<211> LENGTH: 447
<212> TYPE: PRT
<213> ORGANISM: Artificial Sequence
<220> FEATURE:
<223> OTHER INFORMATION: Synthetic

<400> SEQUENCE: 44

-continued

```
Glu Val Lys Leu Val Glu Ser Gly Pro Gly Leu Val Ala Pro Ser Gln
1               5                   10                  15

Ser Leu Thr Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp His Asn Gly Ser Thr Asp Tyr Asn Ser Ala Leu Arg
    50                  55                  60

Ser Arg Leu Ser Ile Asn Lys Asp Lys Ser Lys Asn Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Arg Ser Pro Trp Phe Pro Tyr Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

His Asn His Tyr Thr Gln Lys Ser Leu Ser Leu Ser Pro Gly Lys
            435                 440                 445

<210> SEQ ID NO 45
<211> LENGTH: 330
<212> TYPE: PRT
<213> ORGANISM: Artificial Sequence
<220> FEATURE:
<223> OTHER INFORMATION: Synthetic

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 219
<212> TYPE: PRT
<213> ORGANISM: Artificial Sequence
<220> FEATURE:
<223> OTHER INFORMATION: Synthetic

<400> SEQUENCE: 46

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Asn Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 47
<211> LENGTH: 107
<212> TYPE: PRT
<213> ORGANISM: Artificial Sequence
<220> FEATURE:
<223> OTHER INFORMATION: Synthetic

<400> SEQUENCE: 47

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105

<210> SEQ ID NO 48
<211> LENGTH: 219
<212> TYPE: PRT
<213> ORGANISM: Artificial Sequence
<220> FEATURE:
<223> OTHER INFORMATION: Synthetic

<400> SEQUENCE: 48

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Asp Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```